(12) United States Patent
Palczewski et al.

(10) Patent No.: US 9,907,762 B2
(45) Date of Patent: Mar. 6, 2018

(54) STABILIZED MUTANT OPSIN PROTEINS

(71) Applicants: University of Washington, Seattle, WA (US); Regents of the University of Minnesota, Minneapolis, MN (US)

(72) Inventors: Krzysztof Palczewski, Bellevue, WA (US); Shalesh Kaushal, Gainesville, FL (US); Vladimir Kuksa, Seattle, WA (US); Syed M. Noorwez, Gainesville, FL (US)

(73) Assignees: UNIVERSITY OF WASHINGTON, Seattle, WA (US); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 83 days.

(21) Appl. No.: 14/845,761

(22) Filed: Sep. 4, 2015

(65) Prior Publication Data

US 2016/0045453 A1    Feb. 18, 2016

Related U.S. Application Data

(63) Continuation of application No. 13/217,128, filed on Aug. 24, 2011, now Pat. No. 9,149,446, which is a continuation of application No. 10/801,078, filed on Mar. 15, 2004, now abandoned.

(60) Provisional application No. 60/455,182, filed on Mar. 14, 2003.

(51) Int. Cl.

| | |
|---|---|
| *A61K 31/11* | (2006.01) |
| *A61K 31/07* | (2006.01) |
| *A61K 38/17* | (2006.01) |
| *A61K 31/382* | (2006.01) |
| *A61K 31/435* | (2006.01) |
| *A61K 31/695* | (2006.01) |
| *A61K 9/00* | (2006.01) |

(52) U.S. Cl.
CPC ............ *A61K 31/11* (2013.01); *A61K 9/0048* (2013.01); *A61K 31/07* (2013.01); *A61K 31/382* (2013.01); *A61K 31/435* (2013.01); *A61K 31/695* (2013.01); *A61K 38/1709* (2013.01); *Y10S 514/912* (2013.01)

(58) Field of Classification Search
None
See application file for complete search history.

(56) References Cited

U.S. PATENT DOCUMENTS

| | | | |
|---|---|---|---|
| 3,196,078 A | 7/1965 | Chatzinoff et al. | |
| 3,517,067 A | 6/1970 | Stern | |
| 5,457,135 A | 10/1995 | Baranowitz et al. | |
| 5,620,970 A | 4/1997 | Han et al. | |
| 5,837,728 A | 11/1998 | Purcell | |
| 5,869,468 A | 2/1999 | Freeman | |
| 6,300,328 B1 | 10/2001 | Klimko | |
| 6,552,009 B2 | 4/2003 | Achkar | |
| 6,696,069 B2 | 2/2004 | Harichian et al. | |
| 7,566,808 B2 | 7/2009 | Rando | |
| 7,951,841 B2 | 5/2011 | Palczewski et al. | |
| 8,324,270 B2 | 12/2012 | Maeda et al. | |
| 8,962,691 B2 | 2/2015 | Palczewski et al. | |
| 9,149,446 B2 | 10/2015 | Palczewski et al. | |
| 9,162,978 B2 | 10/2015 | Palczewski et al. | |
| 9,169,204 B2 | 10/2015 | Palczewski et al. | |
| 9,174,936 B2 | 11/2015 | Palczewski et al. | |
| 9,233,091 B2 | 1/2016 | Maeda et al. | |
| 2002/0028849 A1 | 3/2002 | Godkin et al. | |
| 2003/0215413 A1 | 11/2003 | Fares et al. | |
| 2003/0228277 A1 | 12/2003 | Gehlsen | |
| 2004/0022766 A1 | 2/2004 | Acland et al. | |
| 2004/0097587 A1 | 5/2004 | Arbiser | |
| 2004/0242704 A1 | 12/2004 | Palczewski et al. | |
| 2006/0167088 A1 | 7/2006 | Widder et al. | |
| 2006/0281821 A1 | 12/2006 | Palczewski et al. | |
| 2008/0221208 A1 | 9/2008 | Palczewski et al. | |
| 2008/0275133 A1 | 11/2008 | Schwartz et al. | |
| 2010/0035986 A1 | 2/2010 | Maeda et al. | |
| 2011/0034554 A1 | 2/2011 | Washington | |
| 2011/0288170 A1 | 11/2011 | Palczewski et al. | |
| 2012/0041073 A1 | 2/2012 | Palczewski et al. | |
| 2012/0322891 A1 | 12/2012 | Palczewski et al. | |
| 2013/0072443 A1 | 3/2013 | Palczewski et al. | |
| 2013/0072556 A1 | 3/2013 | Palczewski et al. | |
| 2013/0072557 A1 | 3/2013 | Maeda et al. | |
| 2013/0072558 A1 | 3/2013 | Maeda et al. | |

(Continued)

FOREIGN PATENT DOCUMENTS

| | | |
|---|---|---|
| CA | 2601278 A1 | 9/2005 |
| CN | 1169854 A | 1/1998 |

(Continued)

OTHER PUBLICATIONS

Wang et al., Gene mutations in retinitis pigmentosa and their clinical implications, Clin Chim Acta. Jan. 2005;351(1-2):5-16.*
Brogan et al., "Altered retinoid homeostasis catalyzed by a nicotine metabolite: implications in macular degeneration and normal development", Proc. Natl. Acad. Sci. USA, vol. 102, No. 30, pp. 10433-10438 (2005).
Ablonczy et al., "11-cis-retinyl reduces constitutive phosphorylyzation and improves quantum catch in retinoid-deficient mouse rod photoreceptors", J. Biol. Chem., vol. 277, pp. 40491-40498 (2002).
Acland et al., "Gene therapy restores vision in a canine model of childhood blindness", Nature Genetics, vol. 28, pp. 92-95 (2001).

(Continued)

*Primary Examiner* — Gigi Huang
(74) *Attorney, Agent, or Firm* — Jacqueline F. Mahoney; Judy M. Mohr; McDermott Will & Emery LLP

(57) ABSTRACT

Methods and compositions for stabilizing opsin protein, such as a Pro23His mutant opsin protein, in a vertebrate visual system, by administration of opsin-binding synthetic retinoids, are provided. The mutant opsin protein binds to the synthetic retinoid, which stabilizes the mutant opsin protein and/or ameliorates the effects of the mutant opsin protein on the vertebrate visual system.

10 Claims, 7 Drawing Sheets

(56) References Cited

U.S. PATENT DOCUMENTS

| | | | |
|---|---|---|---|
| 2013/0072559 | A1 | 3/2013 | Palczewski et al. |
| 2013/0072560 | A1 | 3/2013 | Palczewski et al. |
| 2013/0072561 | A1 | 3/2013 | Maeda et al. |
| 2013/0072568 | A1 | 3/2013 | Palczewski et al. |
| 2013/0072569 | A1 | 3/2013 | Palczewski et al. |
| 2013/0079403 | A1 | 3/2013 | Palczewski et al. |
| 2013/0196950 | A1 | 8/2013 | Palczewski et al. |

FOREIGN PATENT DOCUMENTS

| | | |
|---|---|---|
| CN | 1455780 A | 11/2003 |
| CN | 1988898 A | 6/2007 |
| EP | 0803248 A2 | 10/1997 |
| GB | 1449027 | 9/1976 |
| GB | 1526410 A | 9/1978 |
| JP | 61/275266 A | 5/1986 |
| JP | 6340525 A | 12/1994 |
| JP | 8198746 A | 8/1996 |
| RU | 2106843 | 3/1998 |
| WO | WO 96/24344 | 8/1996 |
| WO | WO 99/09969 | 3/1999 |
| WO | WO 99/29315 A | 6/1999 |
| WO | WO 00/68364 A2 | 11/2000 |
| WO | WO 02/055540 A1 | 7/2002 |
| WO | WO 02/058586 A2 | 8/2002 |
| WO | WO 02/066068 A2 | 8/2002 |
| WO | WO 02/082904 A2 | 10/2002 |
| WO | WO 03/059336 A1 | 7/2003 |
| WO | WO 2004/082622 A2 | 9/2004 |
| WO | WO 2005/079774 A2 | 9/2005 |
| WO | WO 2006/002097 A2 | 1/2006 |
| WO | WO 2006/033734 A2 | 3/2006 |

OTHER PUBLICATIONS

Acland et al., "Long-term restoration of rod and cone vision by single dose rAAV-mediated gene transfer to the retinain a canin model of childhood blindness", Mol. Ther., vol. 12, No. 6, pp. 1072-1082 (2005).
Aggarwal et al., "2-Halogeno-1,3,dithiane 1 ,3-dioxide; a diastereroselective carbonyl anion equivalent in reactiosn with aldehydes", J. Chem. Soc., vol. 1, pp. 11-19 (1997).
Albeck et al., "Factors Affecting the Absorption Maxima of Acidic Forms of Bacteriohodopsin", Biophys. J., vol. 56, pp. 1259-1265 (1989).
Aleman et al., "Impairment of the transient papillary light reflex in Rpe65(-/-) mice and humans with leber congenital amaurosis", Invest. Opthalmol. Vis. Sci., vol. 45, No. 4, pp. 1259-1271 (2004).
Ames et al., "Biomedical studies on vitamin A. XIV. Biopetencies of Geometric Isomers of Vitamin in the Rat", J. Am Chem. Soc., vol. 77, pp. 4134-4136 (1955).
Asato et al., "Flourinated rhodopsin analogues from 10-flouro- and 14-flouroretinal", J. Am Chem. Soc., vol. 100, No. 18, pp. 5957-5960 (1978).
Baehr et al., "The retinoid cycle and retinal disease", Vision Research, vol. 43, pp. 2957-2958 (2003).
Batten et al., "Lecithin-retinol acyltransferase is essential for accumulation of all-trans-retinyl esters in the eye and in the liver" The Journal of Biological Chemistry, vol. 279, No. 11, pp. 10422-10432 (2004).
Batten et al., "Pharmacological and rAAV gene therapy rescue of visual functions in a blind mouse model of leber congenital amaurosis", PLoS Medicine, vol. 2, Issue. 11, No. e333, pp. 1177-1189 (2005).
Beischel et al., "Azidotetrafluorophenyl retinal analogue: synthesis and bacteriorhodopsin pigment formation", Photochemistry and Photobiology, vol. 60, No. 1, pp. 64-68 (1994).
Bernstein et al., "Biochemical characterization of the retinoid isomerase system of the eye", J. Biol. Chem., vol. 262, No. 35, pp. 16848-16857 (1987).

Berson et al., "A randomized trial of vitamin A and vitamin E supplementation for retinitis Pigmentosa", Arch. Opthamol., vol. 11, pp. 761-772 (1993).
Berson et al., "Retintis pigmentosa: unfolding its mystery", Proc. Natl. Sci. USA, vol. 93, pp. 4526-4528 (1996).
Berson, "Treatment of retinitis Pigmentosa with vitamin A", Digital J. Opthamol. vol. 4, No. 7 Massachusetts Eye and Ear Infirmary, Harvard Medical School (1998).
Berson et al., "Disease progression in patients with dominat retinitis pigmentosa and rhodopsin mutations", Invest. Opthalmol. Vis. Sci., vol. 43, No. 9, pp. 3027-3036 (2002).
Biesalkski et al., "Sensitive Analysis of Retinyl Esters by Isocratic Adsorption Chromatography", J. Clin. Chem. Clin. Biochem., vol. 27, No. 2, pp. 657-74 (1989) *Abstract only*.
Birnbach et al., "Retinoic acid accelerates photoreceptor cell death by apoptosis in Pro23HIS rhodopsin transgenic mice", Invest. Ophtalmol. Vis. Sci., vol. 38, No. 4, pp. s311 (1997).
Boehm et al., "Photoaffinity labeling studies of bacteriohodopsin with [15-$^3$h]-3-Diazo-4-keto-all-trans-retinal", J. Am. Chem. Soc., vol. 112, pp. 7779-7782 (1990).
Borhan et al., "Chemoenzymatic synthesis of 1-cis-retinal photoaffinity analog by use of squid retinochrome", J. Am. Chem. Soc., vol. 119, pp. 5758-5759 (1997).
Borhan et al., "Efficient synthesis 11-cis-retinoids", Chem. Eur. J., vol. 5, No. 4, pp. 1172-1175 (1999).
Bridges, "Vitamin A* and the Role of the Pigment Epithelimn during Bleaching and Regeneration of Rhodopsin in the Frog Eye", Exp. Eye Res., vol. 22, pp. 435-455 (1976).
Buczylko et al., "Mechanisms of opsin activation", J. Biol. Chem., vol. 271, No. 34, pp. 20621-20630 (1996).
Caldwell et al., "Synthesis of retinals with eight- and nine-membered rings in the side chain, models for rhodopsin photobleaching intermediates", J. Org. Chem., vol. 59, pp. 3533-3537 (1993).
Capecchi, "Altering the genome by homologous recombination", Science, vol. 244, No. 4910, pp. 1288-1292 (1989).
Carney and Russell, "Correlation of Dark Adaptation Test Results with Serum Vitamin A Levels in Diseased Adults", J. Nutr., vol. 110, pp. 552-557 (1980).
Caruso et al, "Effects of fenretinide (4-HPR) on dark adaptation", XP002476887; STN Database Accession No. 1998:418096 & Archives of Ophthalmology (Chicago), vol. 116, No. 6, pp. 759-763, CODEN: AROPAW; ISSN:0003-9950, (1998) *Abstract only*.
Chan et al., "Delayed dark adaption caused by nilutamide", J. Neuro-Opthalmology, vol. 28, No. 2, pp. 158-159 (2008).
Chapple et al., "Looking at protein misfolding neurodegenerative disease throuogh retinitis pigmentosa", ACNR, vol. 3, Issue 1, pp. 12-13 (2003).
Chatzinoff et al., "Eleven-cis vitamin A in the treatment of retinits Pigmentosa", Arch. Opthalmol., vol. 80, pp. 417-419 (1968).
Chen et al., "Inherent instability of the retinitis pigmentosa P23H mutant opsin", JBC Papers in Press, Manuscript M114.551713, 31 pages, Latest version can be accessed at http://www.jbc.org/cgi/doi/10.1074/jbc.M114.551713, Published Feb. 10, 2014.
Cideciyan et al., "Rod and cone visual cycle consequences of a null mutation in the 11-cis-retinol dehydrogenase gene in man", Vis. Neurosci., vol. 17, No. 5, pp. 667-678 (2000).
Colmenares et al., "11, 12-Difluororhodopisin and related odd-numbered flurorhodopsins, the use of $J_{F,F}$ for following a cis-trans isomerization process", J. Am. Chem. Soc., vol. 121, pp. 5803-5804 (1999).
Congdon et al., "Responsiveness of dark-adaptation threshold to vitamin A and β-carotene supplementation in pregnant and lactating women in Nepal", Am. J. Clin. Nutr., vol. 72, pp. 1004-1009 (2000).
Corson et al., "Sensitization of bleach rod photoreceptors by 11-cis-locked analogues of retinal", PNAS USA, vol. 87, pp. 6823-6827 (1990).
Crescitelli and Pearlman, "Can isorhodopsin be produced in the living rat?", Vision Res., vol. 12, pp. 2515-2525 (1973).
Crescitelli et al., "The spectral properties and photosensitivites of analogue photopigments regenerated with 10- and 14-substituted retinal analogues" Proc. R. Soc. Lond. B, vol. 233, pp. 55-76 (1988).
Crouch et al., "Photo sensitive pigments formed with rat opsin", Investigative Opthalmology, vol. 15, No. 10, pp. 872-875 (1976).

(56) References Cited

OTHER PUBLICATIONS

Crouch and Katz, "The effect of retinal isomers on the ver and erg of vitamin A deprived rats", Vision Res., vol. 31, pp. 109-115 (1980).
Crouch et al., "Inhibition of rhodopsin regeneration of cyclohexyl derivatives", Vision Research, vol. 22, No. 12, pp. 1451-1456 (1982).
Crouch et al., "Opsin pigments formed with acyctic retinal analogues", FEBS, vol. 158, No. 1, pp. 139-142 (1983).
Crouch et al., "Cyclohepatrienylidine analog of 11-cis retinal", Invest. Opthalmol. Vis. Sci., vol. 25, pp. 419-418 (1984).
Crouch, "Yearly review: studies of rhodopsin and bacteriorhodopsin using modified retinals", Photochemistry and Photobiology, vol. 44, No. 6, pp. 803-807 (1986).
De Grip et al., "10 20 methanorhodopsins 7e 9e 13e-10 20 mthanorhodopsin and 7e 9z 13z-10 20 methanorhodopsin 11-cis-locked rhodopsin analog pigments with unusual thermal and photostability", Eur. J. Biochem., vol. 191, No. 1, pp. 211-220 (1990).
Delange et al., "An addition methyl group at the 10-position of retinal dramatically slows down the kinetics of the rhodopsin photocascade", Biochemistry, vol. 37, No. 5, pp. 1411-1420 (1998).
Dorwald, *Side Reactions in Organic Synthesis: A Guide to Succesful Synthesis Design*, Wiley-VCH Verlag GmbH & Co. KGaA, Weinheim, Preface p. IX, (2005).
Drachev et al., "An investigation of the electrochemical cycle of bacteriorhodopsin analogs with the modified ring", Arch. Biochem. Biophys., vol. 270, No. 1, pp. 184-197 (1989).
Driessen et al., "Disruption of the 11-cis-retinol dehydrogenase gene leads to accululation of cis-retinols and cis-retinyl esters", Mol. Cell Biol., vol. 20, No. 12, pp. 4275-4287 (2000).
Ebrey et al., "Properties of several sterically modified retinal analogs and thier photosensitive pigments", Biochemistry, vol. 14, No. 18, pp. 3933-3941 (1975).
European Seach Report From related European Patent Application No. EP 04757476, mailed on Jun. 5, 2008.
European Search Report From Related European Application No. EP 1154402, search completed on Sep. 5, 2011.
European Search Report From Related European Patent Application No. EP 1154404, search completed on Sep. 6, 2011.
European Search Report From Related European Patent Application No. EP 1154534, search completed on Sep. 5, 2011.
Eyring el al., "Assignment and interpretation of hydrogen out-of-plane vibration in the resonance raman spectra on rhodopsin and bathorhodopsin", Biochemistry, vol. 21, pp. 384-393 (1982).
Fan et al., "Isorhodpsin rather than rhodopsin mediates rod function in RPE65 knock-out mice", PNAS, vol. 100, No. 23, pp. 13662-13667 (2003).
Fujimoto et al., "On the bioactive conformation of the rhodopsin chromophore: absolute sense of twist aroun the 6-s-cis bond", Chem. Eur. J., vol. 7, No. 19, pp. 4198-4204 (2001).
Fujimoto et al., "Solution and biologically relevant conformations of enantiomeric 11-cis-locked cyclopropyl retinals", J. Am. Chem. Soc., vol. 124, pp. 7294-7302 (2002).
Fukada et al., "Studies on structure and function of rhodopsin by use of cyclopentafrienylidene 11-cis-locked rhodopsin", Biochemistry, vol. 23, No. 24, pp. 5826-5832 (1984).
Futterman et al., "The composition of liver vitamin A ester and the synthesis of vitamin A ester by liver microsomes", J. Biol. Chem., vol. 239, No. 12, pp. 4077-4080 (1964).
Gaffney et al., "Aging and cone dark adaption", Optom. Vis. Sci., vol. 89, No. 8, pp. 1219-1224 (2012).
Gao and Hollyfield, "Aging of the human retina" Inv. Opth. Vis. Sci., vol. 33, pp. 1-17 (1992).
Gartner et al., "Quantum yield of chapso-solubilized rhodopsin and 3-hydroxy retianl containing bovine opsin", Photochemistry and Photobiology, vol. 54, No. 6, pp. 1047-1055 (1991).
Geroski et al., "Drug delivery for posterior segment eye disease", IOVS, vol. 42, No. 5, pp. 961-964 (2000).

Grant et al., "Treatable forms of retinitis pigmentos associated with systemic neurological disorders", Int. Opthalmol. Clin. vol. 41, No.1, (2001) printed from http://www.ncbi.nlm.nih.gov/pubmed/11198137 on Jan. 14, 2009 *Abstract only*.
Haeseleer et al., "Dual-substrate specificity short chain retinol dehydrogenase from the vertebrate retina", J. Biol. Chem., vol. 277, No. 47, pp. 45537-45546 (2002).
Haig et al., "Vitamin A and Rod-Cone Dark Adaption in Cirrhoses of the Liver", Science, vol. 87, No. 2267, pp. 534-536 (1938).
Han et al., "The C9 methyl group of retinal interacts with glycine-121 in rhodopsin", PNAS, vol. 94, pp. 13442-13447 (1997).
Harvard Health Publications, "The aging eye: preventing and treating eye disease", Harvard Helath Publications, 3 pgs. (2011) printed from http://www.health.harvard.edu/special_health_reports/the_Aging_Eye on Nov. 5, 2011.
Head, "Natural therapies for ocular disorders, part one: diseases of the retina", Alt. Med. Review, vol. 4, No. 5, pp. 342-359 (1999).
Hiraki et al., "Bacteriorhodopsin analog regeneration with 13-desmethyl-13-loderetinal", Biophysical Journal, vol. 83, pp. 3460-3469 (2002).
Hirano et al., "Constrains of opsin structure on the ligand-binding site: studies with ring-fused retinals", Photochemistry and Photobiology, vol. 76, No. 6, pp. 606-615 (2002).
Hisatomi et al., "Critial role of photoreceptor apoptosis in functional damage after retinal detachment", Curr. Eye Res., vol. 24, No. 3, 161-172 (2002) *Abstract only*, 1 pg. printed from http://www.ncbi.nlm.nih.gov/pubmed/12221523.
Howard et al., "Comparative distribution, pharmacokinetics and placental permeabilities of all-trans-retinoic acid, 13-cis-retinoic acid, all-trans-4-oxo-retinoic acid, retinyl acetate and 9-cis-retinal in hamsters", Arch. Toxicol., vol. 63, pp. 112-120 (1989).
Hu et al., "Unbleachable rhodopsin with an 11-cis-locked eight-membered ring retinal: the visual transduction process", Biochemistry, vol. 33, pp. 408-416 (1994).
Huttunen et al., "Prodrug—from Serendipity to Rational Design", Pharmacological Reviews, vol. 63, No. 3, pp. 750-771 (2011).
Illing et al., "A Rhodopsin mutant linked to autosomal dominant retinitis pigmentosa is prone to aggregate and interacts with ubiquitin proteasome system", J. Biol. Chem., vol. 277, No. 37, pp. 34150-34160 (2002).
Imai et al., "Probing for the threshold energy for visual transduction: red-shifted visual pigment analogs from 3-methoxy-3-dehydroretinal and related compounds", Protochemistry and Photobiology, vol. 70, No. 1, pp. 111-115 (1999).
Imamoto et al., "Structure around $C_6$—$C_7$ bond of the chromophore in bathorhodpsin: low-temperature spectroscopy of 6s-cis-locked bicyclic rhodopsin analogs", Biochemistry, vol. 35, pp. 6257-6262 (1996).
Imanishi et al., "Noninvasive two-photon imaging reveals retinyl ester storage structures in the eye", Cell Biol. vol. 164, pp. 373-383 (2004).
International Search Report from related PCT Patent Application No. PCT/US2004/007987 mailed on Dec. 3, 2004, application now published as International Publication No. WO2004/082622, published on Sep. 30, 2004.
International Search Report from related PCT Patent Application No. PCT/US2005/021812 mailed on Dec. 28, 2005, application now published as International Publication No. WO2006/002097, published on Jan. 5, 2006.
International Search Report from related PCT Patent Application No. PCT/US2009/000624 mailed on Nov. 5, 2009, application now published as International Publication No. WO2006/102418, published on Aug. 20, 2009.
Jackson et al., "Aging and scotopic sensitivity", Vis. Res., vol. 38, pp. 3655-3662 (1998).
Jackson et al., "Aging and dark adaptation", Vis. Res. vol. 39, pp. 3975-3982 (1999).
Jackson et al., "Photoreceptor degeneration and dysfunction in aging and age-related maculopathy", Aging Res. Rev., vol. 1, No. 3, pp. 381-396 (2002).
Jacobson et al., "Retinal degenerations with truncation mutations in the cone-rod homeobox (CRX) gene", Invest. Opthalmol. Vis. Sci., vol. 39, No. 12, pp. 2417-2426 (1988).

(56) References Cited

OTHER PUBLICATIONS

Jacobson et al., "Night blindness in Sorsby'fundus dystrophy reversed by vitamin A" Nat. Genet. vol. 11, pp. 27-32 (1985).
Jacobson et al., "Pheontypic Marker for Early Disease Detection in Dominant Late-Onset Retinal Degeneration", IOVS, vol. 42, No. 8, pp. 1882-1890 (2001).
Jacobson et al., "Identifying photoreceptors in blinc eyes caused by RPE65 mutations: Prerequisite for human gene therapy success", PNAS USA, vol. 102, No. 17, pp. 6177-6182 (2005).
Jang, "Mechanism of rhodopsin activation as examined with ring-constrained retinal analogs and the crystal structure of the ground state protein", The Journal of Biological Chemsitry, vol. 276, No. 28, pp. 26148-26153 (2001).
Jang et al., "Characterization of dehydrogenase activity responsive for oxidation of 11-cis-retinol in the retinal pigment epithelium of mice with a disrupted RDH5 gene. A model for the human heredity disease fundus albunctatus", J. Biol. Chem., vol. 276, No. 35, pp. 32456-32465 (2001).
Jin et al., "Noncovalent occupancy of the retinal-binding pocket of opsin diminsihes bleaching adaptation of retinal cones", Neuron, No. 11, pp. 513-522 (1993).
Karnaukhova et al., "Bioactivity of visual pigments with sterically modified retinal analogs", Bioorganic Chemistry, vol. 27, pp. 372-382 (1999).
Kefalov et al., "Role of nocovalent binding of 11-cis-retinal to opsin in dark adaptation of rod and cone photoreceptors", Neuron, vol. 29, Issue 3, pp. 749-755 (2001).
Kemp et al., "Visual Function and Rhodopsin Levels in Human with Vitamin A Deficiencey", Exp. Eye Res., vol. 46, pp. 185-197 (1988).
Kirillova et al., "Cyclopentene and cyclohexene retinal analogs react differently with bacterioopsin", Chemical Abstracts, vol. 120, pp. 557, (1994) Abstract No. 128:187138 *Abstract only.*
Koenekoop et al., "Oral 9-cis retinoid for childhood blindness due to Leber congenital amaurosis caused by RPE65 or LRAT mutations: an open-label phase 1b trial", Lancet, 8 pages, Published Online http://dx.doi.org/10.1016/S0140-6736(14)60153-7, Published Jul. 14, 2014.
Kubo et al., "Effect of vitamin A palmitate on vitamin A-deficient rabbits", XP002475885; STN Database Accession No. 2000:172779 & Nippon Ganka Gakkai Zasshi, vol. 103, No. 10, pp. 729-733 CODEN:NGZAA6; ISSN: 0029-0203,1999 *Abstract only.*
Kuska et al., "Biochemical and physiological properties of rhodopsin regenerated with 11-cis-6-ring- and 7-ring-retinals", The Jouranl of Biological Chemistry, vol. 2777, No. 44, pp. 42315-42324 (2002).
Kuksa et al., Retinoid cycle in the vertebrate retinal: experimental approaches and mechanisms of isomerization, Vision Research, vol. 43, pp. 2959-2981 (2003).
Kupfer et al., "Information for doctors who follow patients with retinitis pigmentosa", National Eye Institute (1993), printed from http://www.nei.nih.gov/news/clinicalalerts/alert-rp.asp on Jan. 15, 2009, 2 pages.
Kuse et al., "Chage in rod cell function y age-related macular degeneration", Japanese Review of Clinical Opthalmology, vol. 10, No. 100, pp. 59 (2006) *English Abstract.*
Lamb and Pugh, "Dark adaptation and the retinoid cycle of vision", Prog. Retin. Eye Res., vol. 23, pp. 307-380 (2004).
Lamb and Pugh, "Phototransduction, Dark Adaption, and Rhodopsin Regeneration", IOVS, vol. 47, No. 12, pp. 5138-5152 (2006).
Lang, "Ocular drug deliverty conventional ocular formulations", Adv. Drug. Del. Rev., vol. 16, No. 1, pp. 39-43 (1995).
Lawson et al., "Retinal analog restoration of photophobic responses in a blind chlmydomonas-reinhardtll mutant evidence for an archaebacterial like chromophore in a eukaryotic rhodopsin", Biophysical Journal, vol. 60, No. 6, pp. 1490-1498 (1991).
Lewin et al., "Synthesis and characterization of trans-, 13-cis, and 11-cis, 13-cis-12-(hydroxymethyl)retinols", J. Org. Chem., vol. 49, pp. 649-652 (1984).
Lewis et al., "Steric barrier to bathrhodopsin decay in 5-demethyl and mesityl analogues of rhodopsin", J. Am. Chem. Soc., vol. 123, pp. 10024-10029 (2001).
Li et al., "Effect of vitamin A supplementation on rhodopsin mutants threonine-17→methionine and proline-347→serine in transgenic mice and in cell cultures", Proc. Natl. Acad. Sci. USA, vol. 95, pp. 11933-11938 (1998).
Li et al., "Delivery of 9-cis retinal to photoreceptor from bovine serum albumin", Photochem. Photobiol., vol. 69, No. 4, pp. 500-504 (1999).
Lin et al., "Vibrational Assignment of Torsional Normal Modes of Rhodopsin: Probing Excited-State Isomerization Dynamics along the Reaction $C_{11}$—$C_{12}$ Torsion Coordinate", J. Phys. Chem. B, vol. 102, pp. 2787-2806 (1998).
Liu et al., "The nature of restriction in the binding site of rhodopsin. A model study", J. Am. Chem. Soc., vol. 106, No. 26, pp. 8298-8300 (1984).
Maeda et al., "Evaluation of the role of the retinal g protein-coupled receptor (RGR) in the vertebrate retina in vivo", Journal of Neurochemistry, vol. 85, pp. 944-956 (2003).
Maeda et al., "Improvement in Rod and Cone Function in Mouse Model of *Fundus albipunctatus* after Pharmacologic Treatment with 9-*cis*-Retinal", IOVS, vol. 47, No. 10, pp. 4540-4546 (2006).
Maeda et al., "Effects of long-term administration of 9-cis-retinyl acetate on visual function in mice", Inv. Opth. Vis. Sci., vol. 50, No. 1, pp. 322-332 (2009).
Maeda et al., "QLT91001, a 9-cis-retinal analog, is well-tolerated by retinas of mice with impaired visual cycles", Invest. Opthalmol. Vis. Sci., vol. 54, No. 1, pp. 455-466 (2013).
Marmor et al., "Abipunctate retinopathy with cone dysfunction and no abnormality in RDH5 or RLBP1 genes", Retina, vol. 23, No. 4, pp. 543-546 (2003).
Massoud et al., "Plasma vitamin A and beta-carotene in retinitis pigmentosa", Brit. J. Opthal., vol. 59, pp. 200-204 (1975).
Mata et al., "Substrate specificity of retinyl ester hydrolase activity in retinal pigment epithelium", Journal of Lipid Research, vol. 39, pp. 604-612 (1998).
Matsukawa et al., "Role of purpurin as a retinal-binding protein in goldfish retinal during the early stage of optic nerve regeneration: Its priming action on neurite outgrowth", J. Neurosci., vol. 24, No. 38, pp. 8346-8353 (2004).
Maugard et al., "Enzymatic synthesis of derivatives of vitamin A in organic media", J. Mol. Cat. B, vol. 8, pp. 275-280 (2000).
Maugard et al., "Synthesis of water-soluble retinol derivatives by enzymatic method", Biotechnol Prog. vol. 18, pp. 424-428 (2002).
Maxwell et al., "Photodynamic responses in rhodotorula glutinis in the abscense of added sensitizers", Photochemistry and Photobiology, vol. 13, No. 3, pp. 259-273 (1971).
Mayo Clinic, "Retinal detachment", 8 pgs. (2010) reprinted from http://www.mayoclinic.com/health/retinal-detachment/DS00254/METHOD=print&DSECTION=all.
McBee et al., "Isomerization of 11-cis-retinoids to all-trans-retinoids in vitro and in vivo", J. Biol. Chem., vol. 276, No. 51, pp. 48483-48493 (2001).
McBee et al., "Confronting complexity: the interlink of phototransduction and retinod metabolism in the vertebrate retina", Prog. Ret. Eye Res., vol. 20, No. 4, pp. 469-529 (2001).
MedlinePlus, "Diabetic retinopathy", 4 pgs. (2011) printed from http://www.nim.nih.gov/medlineplus/ency/article/00212.htm.
Mendes et al., "Pharmacological manipulation of rhodopsin retinits pigmentosa", Advances in Experimental Medicine in Biology, Chapter 36, pp. 317-323, DOI 10.1007/978-1-4419-1399-9_36, Springer Science+Business Media, LLC (2010).
Mizukami et al., "Photoisomerization mechanism of the rhodopsin chromophore: picosecond photolysis of pigment containing 11-cis-locked eight-membered ring retinal", PNAS, vol. 90, pp. 4072-4076 (1993).
Morimura et al., "Mutations in the RPE65 gene in patients with autosomal recessive retinitis pigmentosa or Leber congenital amaurosis", PNAS USA, vol. 95, pp. 3088-3093 (1998).
Nakamura et al., "A high association with cone dystrophy in fundus albipunctatus caused by mutations of the RDH5 gene", Invest. Opthalmol. Vis. Sci., vol. 41, No. 12, pp. 3925-3932 (2000).

(56) References Cited

OTHER PUBLICATIONS

Newton et al., "Structure-Activity Relationship of Retinoids in Hamster Tracheal Organ Culture", Cancer Res., vol. 40, pp. 3413-3425 (1980).
Nishiguchi et al., "A novel mutations (I143NT) in guanylate cyclase-activating protein 1 (GCAP1) associated with autosomal dominant cone degenerations", Invest. Opthalmol. Vis. Sci., vol. 45, No. 11, pp. 3863-3870 (2004).
Noell "Suitabilitly of retinol, retinal and retinyl palmitate for the regeneartion of bleached rhodopsin in the isolated frog retina", XP002486105, STN Database Accession No. 1985:164043 & Vision Research, vol. 24, No. 11, pp. 1615-1622, CODEN:VISRAM; ISSN:0042-6989, (1984) Abstract only.
Noorwez et al., "Pharmacological chaperone-mediated in vivo folidng and stabilization of the P23H-opsin mutant associated with autosomnal dominat retinitis Pigmentosa", J. Biol. Chem., vol. 278, No. 16, pp. 14442-14450 (2003).
Noorwez et al., "Retinoids assist the cellular folding of the autosomal dominat retinitis Pigmentosa opsin mutant P23H", J. Biol. Chem., vol. 279, No. 16, pp. 16278-16284 (2004).
Norum and Blomhoff, "McCollum Award Lecture, 1992: Vitamin A absorption, transport, cellular uptake, and storage", Am. J. Clin. Nutr., vol. 56, pp. 735-744 (1992).
O'Byrne et al., "Retinoid adsoption and storage in impaired in mice lacking lecithin: retinol acyltransferase (LRAT)", J. Biol. Chem., vol. 280, pp. 35647-35657 (2005).
Ohgane et al., "Retinobenzaldehydes as proper-traficking inducers of folding-defective p23H rhodopsin mutant responsible for retinitis pigmentosa", Bioorg. Med. Chem., vol. 18, No. 19, pp. 7022-7028 (2010).
Owsley et al., "Delays in rod-mediated dark adaption in early age-related maculopathy", Opthalmology, vol. 108, pp. 1196-1202 (2001).
Owsley et al, "Effect of short-term, high-dose retinol on dark adaptation in agingand early age-related maculopathy", Invest. Ophthalmol. Vis. Sci., vol. 47, No. 4, pp. 1310-1318 (2006).
Paik et al., "9-cis-retinoids: biosynthesis of 9-cis-retinoic acid", Biochemistry, vol. 39, No. 27, pp. 8073-8084 (Jul. 2000) Abstract only.
Parry et al., "Visual pigment reconstitution in intact goldfish retinal using synthetic retinaldehyde isomers", Vision research, vol. 40, No. 17, pp. 2241-2247 (2000).
Perusek and Maeda, "Vitamin A Derivatives as Treatment Options for Retinal Degenerative Disease", Nutrients, vol. 5, pp. 2646-2666 (2013).
Price et al., "Mislocation and degradation of human P23H-Rhodopsin-GFP in a knockin mouse model of retinits pigmentosa", Inv. Opth. Vis. Sci., vol. 52, No. 13, pp. 9728-9736 (2011).
Radomska et al., "The use of some ingredients for microemulsion preparation containing retinol and its esters", XP002475886, STN Database Accession No. 2000:139945 & International Journal Of Pharmaceutics, vol. 196, No. 2, pp. 131-134 CODEN:IJPHDEI; ISSN; 0378-5173, (2000) Abstract only.
Rao et al., "Isomers of 3 7 11 trimethlododeca-2 4 6 8 10-pentaenal A linear analog or retinal and lower homologues in their interaction whto bovine opsin and bacterioopsin", Photochemistry and Photobiology, vol. 41, No. 2, pp. 171-174 (1985).
Rao et al., "5-(Trifluoromethyl)bacteriorhodopsin does not translocate protons", J. Am. Chem. Soc., vol. 108, pp. 6077-6078 (1986).
Rao et al., "Regioselective photo isomerization of retinolacetate" Tetrahedron Letter, vol. 21, No. 24, pp. 3441-3444 (1990).
Redmond et al., "Rpe65 is necessary for production of 11-cis-vitamin A in the retinal visual cycle", Nature Genetics, vol. 20, pp. 344-351 (1998).
Reid et al., "Mass Specral Analysis of Eleven Analogs of Vitamin A1", Lipids, vol. 6, No. 1, pp. 558-565 (1973).
Remington: The Science and Practive of Pharmacy, 19$^{th}$ Edition, Gennaro et al., Ed., Mack Publishing Company, pp. 1528-1529 (1995).
Renk, "A rhodopsin pigment containing a spin-labeled retinal", J. Am. Chem. Soc., vol. 109, pp. 6163-6168 (1987).
Rezabek et al., "Effects of dietary retinyl acetate on the promotion of hepatic enzyme-altered foci by polybrominated byphenyls in initiated rats", Food Chem. Toxicol., vol. 27, No. 8, pp. 539-544 (1989) Abstract only.
Robinson et al, "Opsins with mutations at the site of chromphore attachment constituitively activate transducin but are not phosphorylated by rhodopsin kinase", Proc. Natl. Acad. Sci. USA, vol. 91, No. 12, pp. 5411-5415 (1994).
Rotenstreich et al., "Treatment of a retinal dystrophy, fundus albipunctatus, with oral 9-cis-b-carotine", Br. J. Optalmol., vol. 94, pp. 616-621 (2010).
Rotenstreich et al., "Treatment with 9-cis β-carotene-rich powder in patients with retinitis pigmentosa: a randomized crossover trial", JAMA Opthalmol., vol. 131, No. 8, pp. 985-992 (2013).
Russell, "The vitamin A spectrum: from deficiency to toxicity", Am. J. Clin. Nutr., vol. 71, pp. 878-884 (2000).
Sakami et al., "Probing mechanisms of photoreceptor degeneration in a new mouse model of the common form of autosomal dominat retinitis pigmentosa due to P23H opsin mutations", JBC Papers in Press, Manuscript M110.29759, 29 pages, Latest version can be accessed at http://www.jbc.org/cgi/doi/10.1074/jbc.M110.209759, Published Jan. 11, 2011.
Saliba et al., "The cellular fat of mutant rhodopsin: quality control, degradation and aggresome formation", J. Cell Science, vol. 115, pp. 2907-2918 (2002).
Sandberg et al., "Clincal expression correlates with location of rhodopsin mutations in dominant retinitis Pigmentosa", Invest. Opthalmol. Vis. Sci., vol. 36, No. 9, pp. 1934-1942 (1995).
Sekiya et al., "Effect of modification of the chromophore in retinochrome" Biophysical Chemistry, vol. 56, pp. 31-39 (1995).
Semenova et al., "Systems for deliverty of vitamin A to the retina in retinitis pigmentosa", XP002475884; STN Database Accession No. 2002:438129 & New Insights Into Retinal Degerative Diseases, [Proceedings Of The International Sysmposium On Retinal Degeneration], 9th Durango, Co, United States, (2000), Meeting Date (2000), pp. 105-110; Editor (Anderson & Lavail), (2001) Abstract only.
Semenova et al., "Stabilization of all-trans-retinol by cyclodextrins: a comparative study using HPLC and fluorescence spectroscopy", XP002475883; STN Database Accession No. 2003:494986 & Journal Of Inclusion Pheonomean And Macroclyclic Chemistry, Volume Date (2002), vol. 44, No. 1-4, pp. 155-158 CODEN:JIPCF5; ISSN:1388-3127, (2003) Abstract only.
Semple-Rowland et al., "A null mutation in the photoreceptor guanylate cyclase gene causes the retinal degeneration chicken phenotype", Proc. Natl. Acad. Sci. USA, vol. 95, No. 3, pp. 1271-1276 (1998).
Sen et al., "Synthesis and binding studies of a photoaffinity label for bovine rhodopsin", J. Am. Chem. Soc., vol. 104, pp. 3214-3216 (1982).
Sibulesky et al., "Safety of<7500 RE (<2500 IU) vitamin A daily in adults with retinitis Pigmentosa", Am. J. Clin. Nutr., vol. 69, pp. 656-663 (1999).
Sokal et al., "GCAP1 (Y99C) mutatnt is constitutively active in autosomal dominat cone dystrophy", Mol. Cell. vol. 2, No. 1, pp. 129-133 (1998).
Spaeth, "Opthalmic Surgery: Principles & Practice, Second Edition", Harcourt Brace Jovanich, Inc., pp. 85-99 (1990).
Stecher et al., "Preferential release of *11-cis-retinol* from retinal pigment epithelial cells in the presence of cellular retinaldehyde-binding protien" The Journal of Biological Chemistry, vol. 274, No. 13, pp. 8577-8585 (1999).
Steinberg et al., "Isomer composition and spectra of the dark and light adapted froms of artificial bacteriorhodopsins", Photochemistry and Photobiology, vol. 54, No. 6, pp. 969-976 (1991).
Supplementary European Search Report From Related European Patent Application No. EP0577356, mailed on Aug. 4, 2008.
Tan et al., "Absolute sense of tweist of the C12—C13 bond of the retinal chromophorein bovine rhodopsin based on exciton-coupled CD spectra of 11, 12-dihydroretinal analogues", Agnew. Chem. Int. Ed. Engl. vol. 36, No. 19, pp. 2089-2093 (1997).

(56) References Cited

OTHER PUBLICATIONS

Tarkhov et al., "Study of a structure-property relationship for retinal derivatives taking into account their confromational flexibility", Chemical Abstracts, vol. 128, 18, pp. 270 (1998) Abstract No. 128:214600 *Abstract only*.

Teller et al., "Advances in determination of a high-resolution three-dimensional structure of rhodopsin, a model of G-protein-coupled receptors (GPCRs)", Biochemisty vol. 40, No. 26, pp. 7761-7772 (2001).

The Eye Digest, "Aging eye in the US", 2 pgs. (2001) printed from http://web.archive.org/web/20060810014820/http://www.agingeye.net/mainnews/usaging.php.

Thomson Scientific, London, GB; AN 1995-063773, XP002475888 & JP 06340525 A (Lion Corp); Dec. 13, 1993 *Abstract only*.

Thomson Scientific, London, GB; AN 1996-408307, XP002475889 & JP 08198746 A (Lion Corp); Aug. 6, 1996 *Abstract only*.

Thomson Scientific, London, GB; AN 1998-518867, XP002475890 & RU 2106843 C1 (Krasy Med Acad); Mar. 20, 1998 *Abstract only*.

Thompson et al., "Mutations in the gene encoding lecithin reteinol acyltransferase are associated with early-onset sever retinal dystrophy", Nat. Genet., vol. 28, pp. 123-124 (2001).

Thompson et al., "Gene defects in vitamin A metabolism of the retinal pigment epithelium", Genetics in Ophthalmology, vol. 37, pp. 141-154 (2003).

Travis et al., "Diseases caused by defects in the visual cycle: retinoids as potential therapeutic agents", Annu. Rev. Pharmacol. Toxicol., vol. 47, pp. 469-512 (2007).

Van Hooser et al., "Rapid restoration of visual pigment and function with oral retinoid in a mouse model of childhood blindness", PNAS, vol. 97, No. 15, pp. 8623-8628 (2000).

Van Hooser et al., "Recovery of visual functions in a mouse model of leber congenital amaurosis", The Journal of Biological Chemistry, vol. 277, No. 21, pp. 19173-19182 (2002).

Vitamin Converter, known vitamin A conversion, 3 pgs., printed from http;//www.robert-forbes.com/resources/vitamincoverter.html on Apr. 19, 2012.

Wada et al., "Retinoids and related compounds. part 26. synthesis of (11Z)-8, 18- propano- and methano-retinals and conformtional study of the rhodopsin chromophore", J. Chem. Soc., vol. 1, pp. 2430-2439 (2001).

Weiser and Somorjai, "Bioactivity of cis and dicis isomers of vitamin A esters", Internatl. J. Vit. Nutr., vol. 62, pp. 201-208 (1992).

Wingerath et al., "Analysis of cyclic and acyclic analogs of retinol, retinoic acid, and retinal by laser desoption Ionization-, matrix-associated laser desorption ionization-mass spectrometry, and UV/Vis spectroscopy", Analyitical Biolchemisty, vol. 272, pp. 232-242 (1999).

Witkovsky et al., "Formation, coversion, and utlitization of isorhodopsin, rhodopsin, and porphyrospsin by rode photoreceptors in the *Xenopus retina*", J. Gen. Physiol., vol. 72, pp. 821-836 (1978).

www.wrongdiagnosis.com, "Symptom: night blindness", pp. 1-13 (Jun. 3, 2008).

Woodward et al., "The inflow and outflow of anit-glaucoma frugs", Trends Pharm. Soc., vol. 25, Issue 5, pp. 238-241 (2004).

Yamamoto et al., "Important role of the proline residue in the signal sequence that directs the secretion of human lysozyme in *Saccharomyces cerevisiae*", Biochemistry, vol. 28, pp. 2728-2732 (1989).

Yamamoto et al., "Mutations in the gene encoding 11-cis retinol dehydrogenase case delayed dark adaption and fundus Albipunctatus", Nat. Genet., vol. 22, No. 2, pp. 188-191 (1999).

Yan et al., "Mechanism of activation of sensory rhodopsin I: evidence for steric trigger", PNAS, vol. 88, pp. 9412-9416 (1991).

Yoshikami et al., "Visial pigments of vitamin A-deficient rat following vitamin A2 administration", Vision Research, vol. 9, No. 6, pp. 633-646 (1969).

Yoshizawa and Wald, "Photochemistry of lodopsin", Nature vol. 215, pp. 566-571 (1967).

Zankel et al., "Bovine rhodopsin with 11-cis-locked retinal chormphore neither activates rhodopsin kiniase nor undergoes conformational change upon irradiation", J. American Chemical Soc., vol. 112, No. 13, pp. 5387-5388 (1990).

Zhang et al., "Structure, alternative splicing, and expression of the human RGS9 gene", Gene, vol. 240, No. 1, pp. 23-24 (1999).

Zhu et al., "A naturallay occuring mutation of the opsin gene (T4R) in dogs affects glycosylation and stability of the G protein-coupled receptor", J. Biol. Chem., vol. 279, No. 51, pp. 53828-53839 (2004).

"Types of AMD", Macular Degeneration Partnership, 8733 Beverly Blvd., Suite201, Los Angeles, CA 90048, Online article downloaded from: http://web.archive.org/web/20030216034002/http://www.amd.org/amd/typesofamd.asp, 3 pages (2003).

"What is AMD?", Macular Degeneration Partnership, 8733 Beverly Blvd., Suite201, Los Angeles, CA 90048, Online article downloaded from: http://web.archive.org/web/20030206231257/http://amd.org/amd/index.asp, 2 pages. (2003).

* cited by examiner

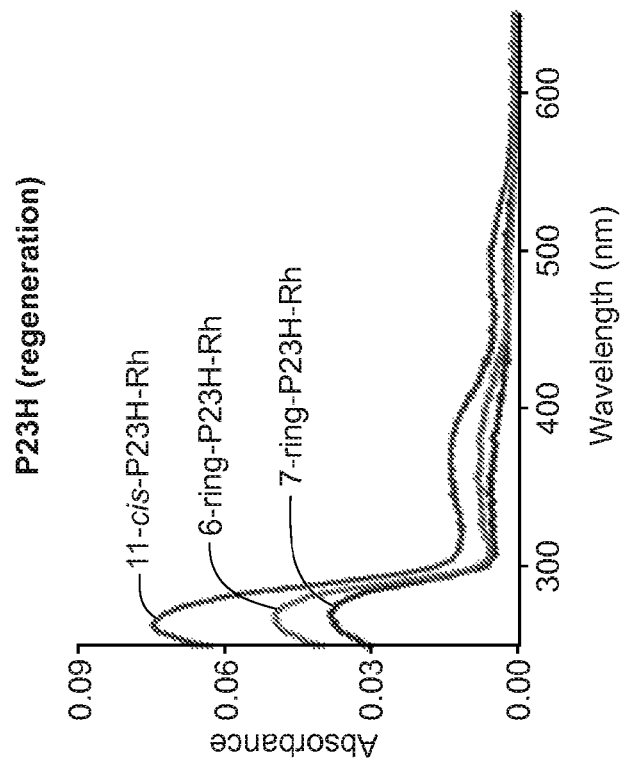
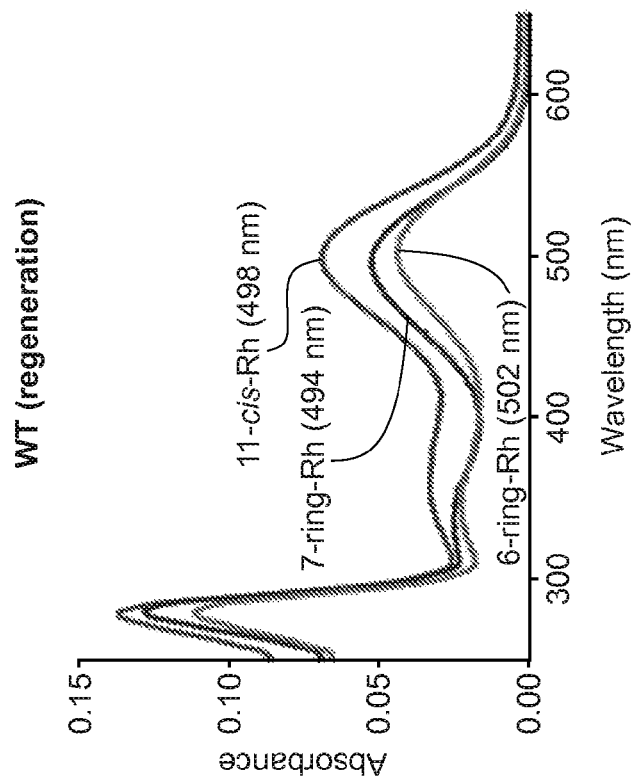
FIG. 2A
FIG. 2B

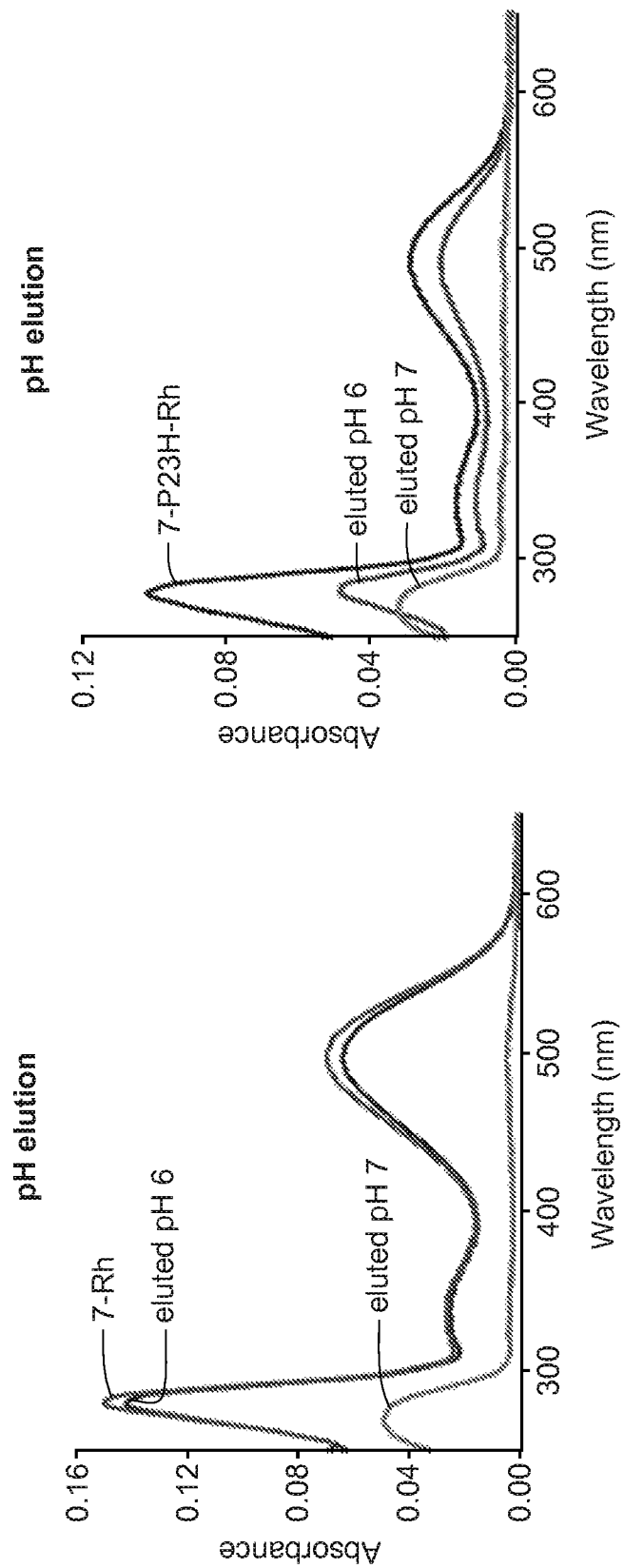

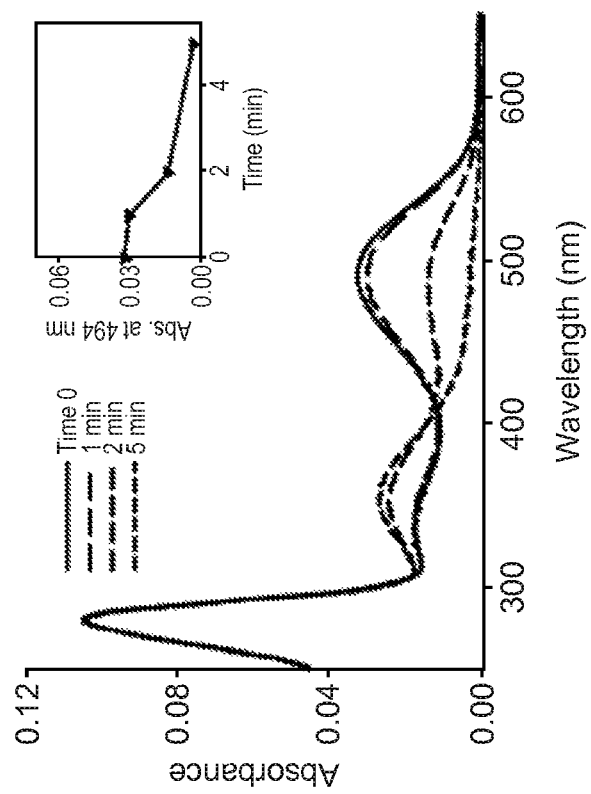
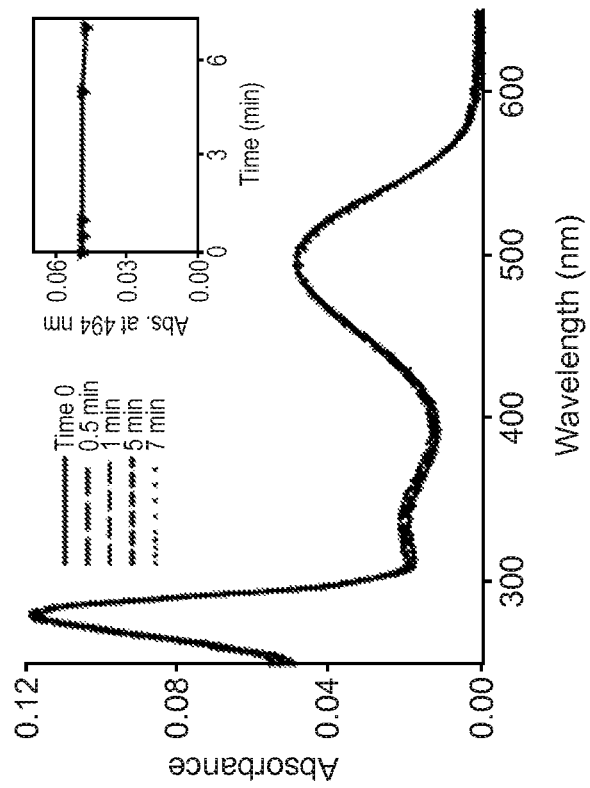
FIG. 3A
FIG. 3B

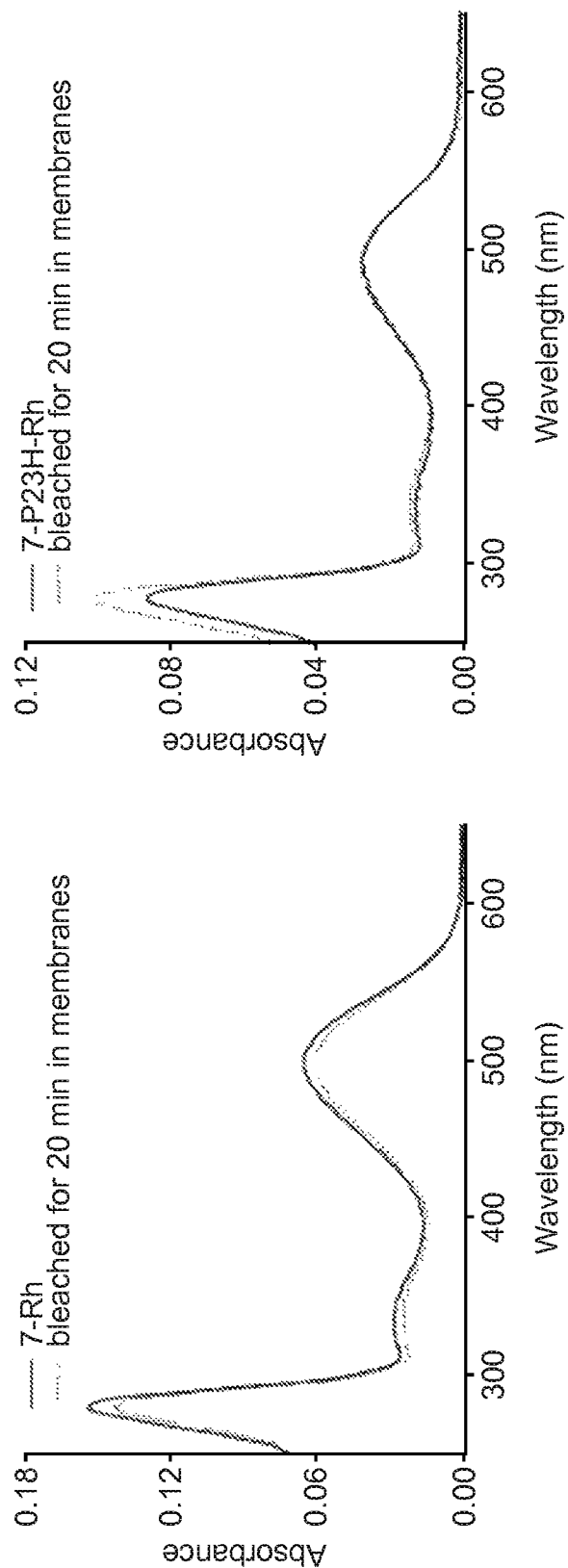

STABILIZED MUTANT OPSIN PROTEINS

CROSS-REFERENCES TO RELATED APPLICATIONS

This application is a continuation of U.S. application Ser. No. 13/217,128, filed Aug. 24, 2011, now U.S. Pat. No. 9,149,446, which is a continuation of U.S. application Ser. No. 10/801,078 filed Mar. 15, 2004, now abandoned, which claims the benefit of U.S. Provisional Patent Application No. 60/455,182, filed Mar. 14, 2003, the disclosures of which are incorporated by reference herein.

STATEMENT REGARDING FEDERALLY SPONSORED RESEARCH OR DEVELOPMENT

This invention was made with government support under grant numbers EY008061 and EY009339 awarded by the National Institutes of Health. The government has certain rights in the invention.

BACKGROUND OF THE INVENTION

A diminished visual acuity or total loss of vision may result from a number of eye diseases or disorders caused by dysfunction of tissues or structures in the anterior region of the eye and/or posterior region of the eye. The eye is divided anatomically into an anterior and posterior segment. The anterior segment includes the cornea, anterior chamber, iris and ciliary body (anterior choroid), posterior chamber and crystalline lens. The posterior segment includes the retina with optic nerve, choroid (posterior choroid) and vitreous. The posterior portion of the eyeball supports the retina, choroid and associated tissues.

Protein conformational disorders are a set of inherited human diseases in which mutant proteins are misfolded. Protein conformation disorders can affect proteins of the vertebrate visual system and cause dysfunction of tissues or structures within the eye. For example, misfolded proteins can aggregate, causing damage within cells expressing the mutant protein. Certain types of retinitis pigmentosa are associated with protein conformational disorders. For example, many opsin mutants associated with retinitis pigmentosa are misfolded and retained within the cell.

Rhodopsin (Rh) is the visual pigment protein of the rod cell and belongs to a large family of transmembrane G protein-coupled receptors, which are involved in numerous physiological functions. This superfamily of membrane glycoprotein receptors is characterized by seven transmembrane α-helices that are anchored within the lipid bilayer. Rhodopsin is composed of opsin, the apoprotein, which is bound to chromophore. In contrast to other G protein-coupled receptors, which respond to diffusible ligands, rhodopsin responds to light. The chromophore in rhodopsin, 11-cis-retinal, is a covalently bound reverse agonist that yields a distinct UV-visible spectrum with a max of approximately 500 nm. Rhodopsin is approximately 40,000 daltons. The crystal structure of rhodopsin has been previously elucidated.

In recent years, more than 100 opsin mutants have been linked to various genetic forms of retinitis pigmentosa, the most common form of hereditary retinal degeneration. Retinitis pigmentosa leads to photoreceptor death and subsequent severe loss of peripheral and night vision. These opsin mutants account for nearly 50% of all the autosomal dominant retinitis pigmentosa cases with the most common being a substitution of Proline 23 to Histidine (P23H), which accounts for approximately 10% of all retinitis pigmentosa cases.

Although opsin mutants display distinct biochemical features, the mutant phenotypes fall mainly into three basic classes. Class I mutants are expressed at nearly wild-type levels and form stable pigment with 11-cis-retinal in the dark. The associated amino acid substitutions cluster at the C terminus of rhodopsin and disrupt vectorial transport to the rod outer segment. Some mutants also inefficiently activate transducin. Class II mutants do not bind 11-cis-retinal and are retained in the endoplasmic reticulum. Class III mutants, like P23H, form small amounts of pigment and mainly remain in the endoplasmic reticulum or form aggresomes. These mutants are typically targeted for degradation by the ubiquitin proteasome system. Other phenotypic properties associated with opsin amino acid substitutions may include the destabilization of the structure formed within the rod outer segment by mutated rhodopsin molecules or the disruption of other biological processes unique to the rod outer segment.

Patients with the P23H substitution usually have milder disease progression than those harboring other rhodopsin mutations. Based on the crystal structure of rhodopsin, Proline 23 is located in the N-terminal tail within one of the β-strands that make up an integral part of the N-terminal plug. The plug keeps the chromophore in its proper position, and mutations within this region result in improper folding of opsin and poor binding of the chromophore. P23H-opsin forms the pigment poorly, does not acquire the Golgi-related glycosylation, and is retained within the cell, collectively providing evidence that it is misfolded.

There is currently no effective treatment for protein conformational disorders of vertebrate visual systems. The present invention satisfies this and other needs.

BRIEF SUMMARY OF THE INVENTION

The present invention provides methods of restoring or stabilizing photoreceptor function in a vertebrate visual system comprising a mutant opsin protein. Mutant opsin proteins can be stabilized by contacting the mutant protein with an opsin-binding synthetic retinoid. The mutant opsin protein binds to the synthetic retinoid, which stabilizes the mutant opsin protein and/or ameliorates the effects of the mutant opsin protein on the vertebrate visual system.

In one aspect, a method is provided for restoring photoreceptor function in a vertebrate eye having a mutant opsin protein. The method generally includes administering to the vertebrate an effective amount of an opsin-binding synthetic retinoid in a pharmaceutically acceptable vehicle. The opsin-binding synthetic retinoid binds to and stabilizes the opsin protein in the eye. The opsin-binding synthetic retinoid can be, for example, an 11-cis-7-ring retinal, a 9-cis-7-ring retinal, cycloheptatrienylidene 11-cis-locked retinal or cycloheptatrienylidene 9-cis-locked retinal. The opsin-binding synthetic retinoid also can be, for example, a synthetic retinoid of formula I, II, III, IV, V, VI, VII, VIII, IX, X, XI, XII or XIII. In another embodiment, the opsin-binding synthetic retinoid is a 9-cis-fused retinal. The mutant opsin protein can be, for example, a Pro23His mutant opsin protein.

The opsin-binding synthetic retinoid can be locally administered to the eye. For example, the opsin-binding synthetic retinoid can be locally administered by eye drops, intraocular injection or periocular injection. The opsin-binding synthetic retinoid also can be orally administered to a subject comprising the vertebrate eye.

In another aspect, a method is provided for stabilizing mutant opsin protein. The method generally includes contacting the mutant opsin protein with an opsin-binding synthetic retinoid for an amount of time sufficient for the formation of a stabilized opsin/synthetic retinoid complex. The opsin-binding synthetic retinoid can be, for example, a synthetic retinoid of formula I, II, III, IV, V, VI, VII, VIII, IX, X, XI, XII or XIII. In certain embodiments, the opsin-binding synthetic retinoid is a 9-cis-locked retinal, an 11-cis-locked retinal, an 11-cis-7-ring retinal or a 9-cis-ring retinal. In certain other embodiments, the opsin-binding synthetic retinoid is cycloheptatrienylidene 11-cis-locked retinal or cycloheptatrienylidene 9-cis-locked retinal. The mutant opsin protein can be, for example, a Pro23His mutant opsin protein.

In yet another aspect, a method of ameliorating loss of photoreceptor function in a vertebrate eye is provided. The method generally includes prophylactically administering an effective amount of an opsin-binding synthetic retinoid in a pharmaceutically acceptable vehicle to a vertebrate eye comprising a mutant opsin protein having a reduced affinity for 11-cis-retinal. The synthetic retinoid binds to and stabilizes the mutant opsin protein.

The opsin-binding synthetic retinoid can be orally administered to a vertebrate. The opsin-binding synthetic retinoid also can be locally administered to the vertebrate eye.

The opsin-binding synthetic retinoid can be, for example, a synthetic retinoid of formula I, II, III, IV, V, VI, VII, VIII, IX, X, XI, XII or XIII. In certain embodiments, the opsin-binding synthetic retinoid can be a 9-cis-7-ring retinal, an 11-cis-7-ring retinal, cycloheptatrienylidene 11-cis-locked retinal or cycloheptatrienylidene 9-cis-locked retinal. The mutant opsin protein can, for example, have mutation (e.g., an amino acid substitution, deletion, insertion, or the like) in the N-terminal plug. For example, the mutant opsin protein can be a Pro23His mutant opsin protein.

In yet another aspect, an ophthalmologic composition including an opsin-binding synthetic retinoid in a pharmaceutically acceptable vehicle is provided. The opsin-binding synthetic retinoid can be, for example, a synthetic retinoid of formula I, II, III, IV, V, VI, VII, VIII, IX, X, XI, XII or XIII. The opsin-binding synthetic retinoid can be, for example, a 9-cis-7-ring retinal, an 11-cis-7-ring retinal, cycloheptatrienylidene 11-cis-locked retinal or cycloheptatrienylidene 9-cis-locked retinal.

In a related aspect, an oral dosage form including an opsin-binding synthetic retinoid in a pharmaceutically acceptable vehicle is provided. The opsin-binding synthetic retinoid can be, for example, a synthetic retinoid of formula I, II, III, IV, V, VI, VII, VIII, IX, X, XI, XII or XIII. The opsin-binding synthetic retinoid can be, for example, a 9-cis-7-ring retinal, an 11-cis-7-ring retinal, cycloheptatrienylidene 11-cis-locked retinal or cycloheptatrienylidene 9-cis-locked retinal.

In yet another aspect, a method of identifying an opsin-binding synthetic retinoid to stabilize a mutant opsin protein is provided. The method generally includes providing an expression system for the expression of a mutant opsin protein, contacting the mutant opsin protein with a synthetic retinoid for a time sufficient and in suitable conditions for the binding of the synthetic retinoid by the mutant opsin protein; and detecting whether the mutant opsin protein binds the synthetic retinoid to form a stable mutant opsin protein/synthetic retinoid complex. The expression system can be, for example, a eukaryotic cell line expressing the mutant opsin protein. The synthetic retinoid can be, for example, administered to cell culture media in which the eukaryotic cell line is cultured. The opsin-binding synthetic retinoid can be, for example, a synthetic retinoid of formula I, II, III, IV, V, VI, VII, VIII, IX, X, XI, XII or XIII.

BRIEF DESCRIPTION OF THE DRAWINGS

FIG. 1A is an illustration of a two-dimensional model of rhodopsin. Shading indicates a mutation associated with retinitis pigmentosa. Proline 23 is shown by shading and the designation "P23. " FIG. 1B shows chemical structures of the four 11-cis-7-ring retinal isomers. Carbon atom numbering is as accepted in retinoid nomenclature.

FIGS. 2A-2F show pigment formation when the chromophores were added to harvested cell membranes or provided during biosynthesis. FIG. 2A is a graph showing regeneration of wild-type rhodopsin in cell membranes with 11-cis-retinal, 11-cis-6-ring retinal, and 11-cis-7-ring retinal. FIG. 2B is a graph showing lack of regeneration of P23H-rhodopsin in cell membranes with 11-cis-retinal, 11-cis-6-ring retinal, and 11-cis-7-ring retinal. FIG. 2C is a graph showing regeneration of wild-type rhodopsin with 11-cis-6-ring retinal, 11-cis-7-ring retinal, and 11-cis-retinal when retinals were added during biosynthesis. FIG. 2D is a graph showing regeneration of P23H-rhodopsin with 11-cis-7-ring retinal and 11-cis-retinal, but not with 11-cis-6-ring retinal, when retinals were added during biosynthesis. Insets in FIGS. 2C and 2D are graphs showing acid denaturation of purified 7-rhodopsin and 11-cis-7-ring-P23H-rhodopsin, respectively. FIG. 2E is a graph showing elution of 7-rhodopsin at pH 6.0 and pH 7.0. FIG. 2F is a graph showing elution of 7-P23H-rhodopsin at pH 6.0 and 7.0.

FIGS. 3A-3D show the photosensitivity of 7-rhodopsin and 7-P23H-rhodopsin in detergent and in cell membrane. FIG. 3A is a graph showing purified 7-rhodopsin is stable to light in detergent. FIG. 3B is a graph showing purified 7-P23H-rhodopsin was bleached after 5 minutes of exposure to light in detergent. FIGS. 3C and 3D are graphs showing 7-rhodopsin and 7-P23H-rhodopsin in cell membranes were not bleached by light. Insets for FIGS. 3A and 3B show changes in absorption at 494 nm as a function of time.

DETAILED DESCRIPTION OF THE INVENTION

Figure 1A:
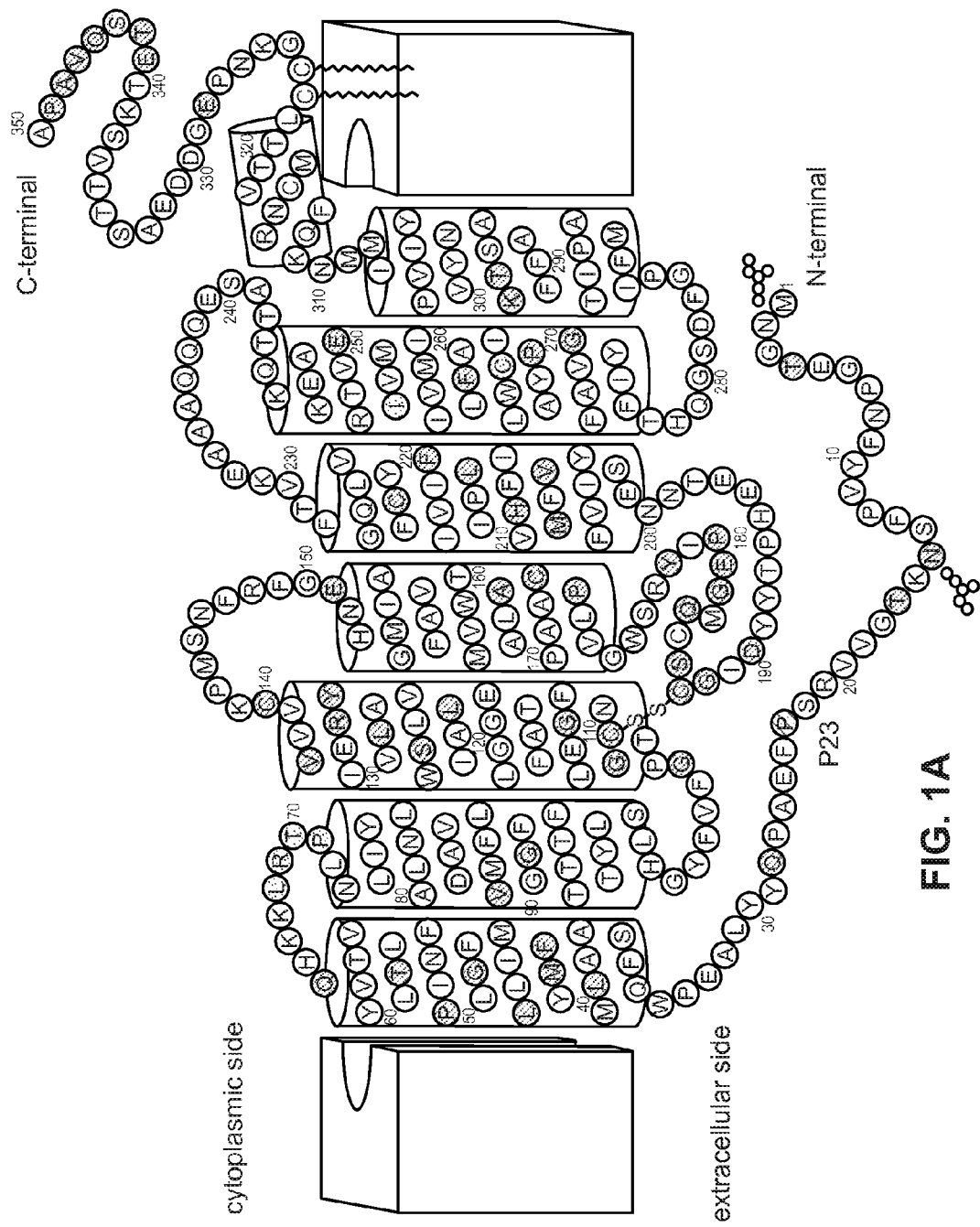
FIGS. 1A-1B are models of rhodopsin and structures of 7-locked-retinals, respectively.

The present invention provides methods of restoring or stabilizing photoreceptor function in a vertebrate visual system having a mutant opsin protein. Mutant opsin proteins can be stabilized by contacting the mutant protein with an opsin-binding synthetic retinoid. The mutant opsin protein binds to the synthetic retinoid, which stabilizes the mutant opsin protein and/or ameliorates the effects of the mutant opsin protein on the vertebrate visual system. An opsin-binding synthetic retinoid can be administered prophylactically or therapeutically to a vertebrate to prevent or reduce damage to the eye associated with the mutant opsin protein. Suitable vertebrates include, for example, human and non-human vertebrates. Suitable non-human vertebrates include, for example, mammals, such as dogs, cats, horses and other domesticated animals.

The mutant opsin protein has one or more amino acid substitutions, deletions, insertions and/or other mutations that affect nascent protein folding, stability, degradation, localization, or the like. Mutant opsin proteins can be, for example, a class I, class II or class III opsin mutant. Typically, the mutant opsin protein exhibits reduced affinity for 11-cis-retinal and/or does not form a stable complex with 11-cis-retinal. In certain embodiments, the opsin mutant is a class III mutant. The opsin mutant also can be, for example, associated with a dominant retinitis pigmentosa condition. In additional embodiments, the opsin mutant comprises an amino acid substitution, insertion and/or deletion in the N-terminal plug of opsin, which results in reduced affinity for 11-cis-retinal. In an exemplary embodiment, the opsin mutant is a Pro23His mutant in human opsin. In additional embodiments, the opsin mutant is a Phe45Leu mutant, a Gly51Val mutant, a Gly51Arg mutant, a Leu125Arg mutant, a Gly114Val mutant, a Gly114Asp mutant, an Ala164Glu mutant, or the like, in human opsin.

The opsin-binding synthetic retinoids are retinals derived from 11-cis-retinal or 9-cis-retinal, or are 9-cis-retinal. In certain embodiments, the "synthetic retinoid" is a "synthetic cis retinoid." Synthetic retinoids according to the present invention can bind to an opsin mutant, and function as a chaperone, or opsin agonist. As used herein, the term "chaperone" refers to a molecule or compound that helps a nascent polypeptide chain fold into the proper conformation, stabilizes the folding protein, protects the nascent polypeptide from making premature or nonproductive contacts, and/or protects the protein from improper modification.

In certain additional embodiments, the synthetic retinoid restores function (e.g., photoreception) to the mutant opsin when it is part of an opsin/synthetic retinoid complex, whereby the mutant opsin/synthetic retinoid complex can respond to photons.

Synthetic retinoids include 11-cis-retinal derivatives or 9-cis-retinal derivatives such as, for example, the following: acyclic retinals; retinals with modified polyene chain length, such as trienoic or tetraenoic retinals; retinals with substituted polyene chains, such as alkyl, halogen or heteratom-substituted polyene chains; retinals with modified polyene chains, such as trans- or cis-locked polyene chains, or with, for example, allene, alkane, alkene or alkyne modifications; and retinals with ring modifications, such as heterocyclic, heteroaromatic or substituted cycloalkane or cycloalkene rings.

In certain embodiments, the synthetic retinoid can be a retinal of the following formula I:

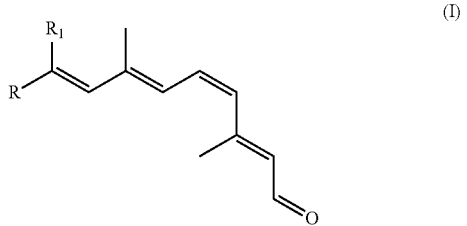

(I)

R and R1 can be independently selected from linear, iso-, sec-, tert- and other branched alkyl groups as well as substituted alkyl groups, substituted branched alkyl, hydroxyl, hydroalkyl, amine, amide, or the like. R and R1 can independently be lower alkyl, which means straight or branched alkyl with 1-6 carbon atom(s) such as methyl, ethyl, propyl, isopropyl, butyl, isobutyl, tert-butyl, pentyl, hexyl, or the like. Suitable substituted alkyls and substituted branch alkyls include, for example, alkyls, branched alkyls and cyclo-alkyls substituted with oxygen, hydroxyl, nitrogen, amide, amine, halogen, heteroatom or other groups. Suitable heteroatoms include, for example, sulfur, silicon, and fluoro- or bromo-substitutions.

In certain additional embodiments, R or R1 can be a cyclo-alkyl such as, for example, hexane, cyclohexene, benzene as well as substituted cyclo-alkyl. Suitable substituted cyclo alkyl include, for example, cyclo-alkyls substituted with oxygen, hydroxyl, nitrogen, amide, amine, halogen, heteroatom or other groups. Suitable heteroatoms include, for example, sulfur, silicon, and fluoro- or bromo-substitutions.

The synthetic retinoid also can be a derivative of an 11-cis-retinal or 9-cis-retinal that has a modified polyene chain length of the following formula II:

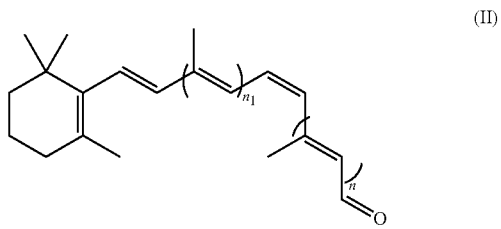

(II)

The polyene chain length can be extended by 1, 2, or 3 alkyl, alkene or alkylene groups. According to formula II, each n and $n_1$ can be independently selected from 1, 2, or 3 alkyl, alkene or alkylene groups, with the proviso that the sum of the n and $n_1$ is at least 1.

The synthetic retinoid also can be a derivative of an 11-cis-retinal or 9-cis-retinal that has a substituted polyene chain of the following formulas, respectively, IIIa and IIIb:

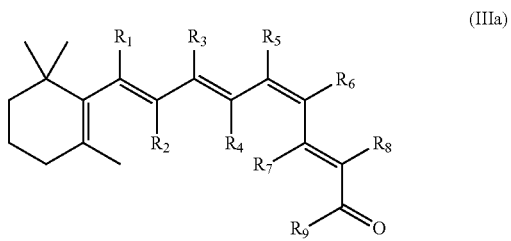

(IIIa)

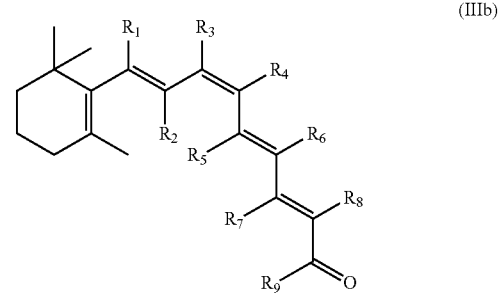

(IIIb)

Each of R1 to R9 can be independently selected from hydrogen, alkyl, branched alkyl, cyclo-alkyl, halogen, a heteroatom, hydroxyl, hydroxyalkyl, amine, amide, or the like. Suitable alkyls include, for example, methyl, ethyl, propyl, substituted alkyl (e.g., alkane with hydroxyl, hydroalkyl, amine, amide) or the like. Suitable branched alkyl can be; for example, isopropyl, isobutyl, substituted branched alkyl, or the like. Suitable cyclo-alkyls can include, for example, cyclohexane, cycloheptane, and other cyclic alkanes as well as substituted cyclic alkanes such as substituted cyclohexane or substituted cycloheptane. Suitable halogens include, for example, bromine, chlorine, fluorine, or the like. Suitable heteroatoms include, for example, sulfur, silicon, and fluoro- or bromo-substitutions. Suitable substituted alkyls, substituted branch alkyls and substituted cyclo-alkyls include, for example, alkyls, branched alkyls and cyclo-alkyls substituted with oxygen, hydroxyl, nitrogen, amide, amine, halogen, a heteroatom or other groups. In exemplary embodiments, the synthetic retinoid is 9-ethyl-11-cis-retinal, 7-methyl-11-cis-retinal, 13-desmethyl-11-cis-retinal, 11-cis-10-F-retinal, 11-cis-10-Cl-retinal, 11-cis-10-methyl-retinal, 11-cis-10-ethyl-retinal, 9-cis-10-F-retinal, 9-cis-10-Cl-retinal, 9-cis-10-methyl-retinal, 9-cis-10-ethyl-retinal, 11-cis-12-F-retinal, 11-cis-12-Cl-retinal, 11-cis-12-methyl-retinal, 11-cis-10-ethyl-retinal, 9-cis-12-F-retinal, 9-cis-12-Cl-retinal, 9-cis-12-methyl-retinal, 11-cis-14-F-retinal, 11-cis-14-methyl-retinal, 11-cis-14-ethyl-retinal, 9-cis-14-F-retinal, 9-cis-14-methyl-retinal, 9-cis-14-ethyl-retinal, or the like.

The synthetic retinoid further can be derivative of an 11-cis-retinal or 9-cis-retinal that has a modified ring structure. Suitable examples include, for example, derivatives containing ring modifications, aromatic analogs and heteroaromatic analogs of the following formulae IV, V and VI, respectively:

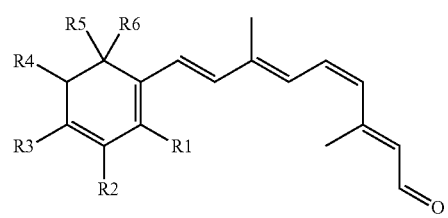

(IV)

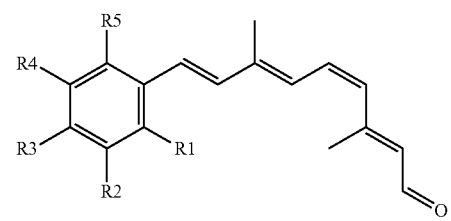

(V)

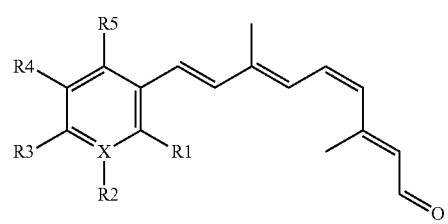

(VI)

Each of R1 to R5 or R6, as applicable, can be independently selected from hydrogen, alkyl, substituted alkyl, hydroxyl, hydroalkyl, amine, amide, halogen, a heteroatom, or the like. Suitable alkyls include, for example, methyl, ethyl, propyl, isopropyl, butyl, isobutyl or the like. Suitable halogens include, for example, bromine, chlorine, fluorine, or the like. Suitable heteroatoms include, for example, sulfur, silicon, or nitrogen. In addition, X can be a heteroatoms, such as, for example, sulfur, silicon, or nitrogen.

The synthetic retinoid can further be a derivative of an 11-cis-retinal or 9-cis-retinal that has a modified polyene chain. Suitable derivatives include, for example, those with a trans/cis locked configuration, 6s-locked analogs, as well as modified allene, alkene, alkyne or alkylene groups in the polyene chain. In one example, the derivative is an 11-cis-locked analog of the following formula VII:

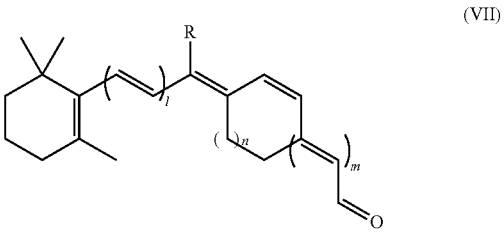

(VII)

R can be, for example, hydrogen, methyl or other lower alkane or branched alkane, or a heteroatom. n can be 0 to 4. m plus 1 equals 1, 2 or 3.

In a specific embodiment, the synthetic retinoid is a 11-cis-locked analog of the following formula VIII:

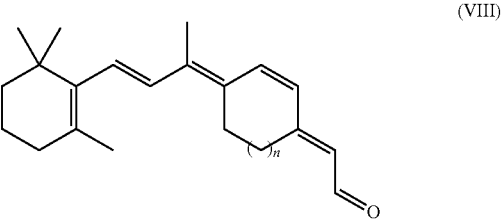

(VIII)

n can be 1 to 4.

In certain exemplary embodiments, the synthetic retinoid is 9,11,13-tri-cis-7-ring retinal, 11,13-di-cis-7-ring retinal, 11-cis-7-ring retinal or 9,11-di-cis-7-ring retinal.

In another example, the synthetic retinoid is a 6s-locked analog of formula IX. R1 and R2 can be independently selected from hydrogen, methyl and other lower alkyl and substituted lower alkyl. R3 can be independently selected from an alkene group at either of the indicated positions.

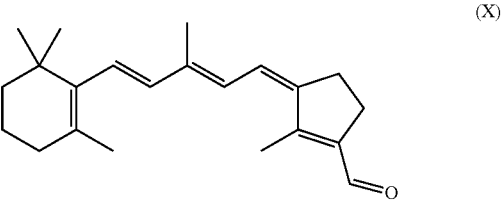

(X)

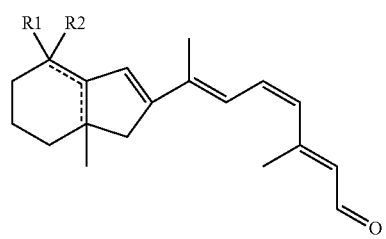

(IX)

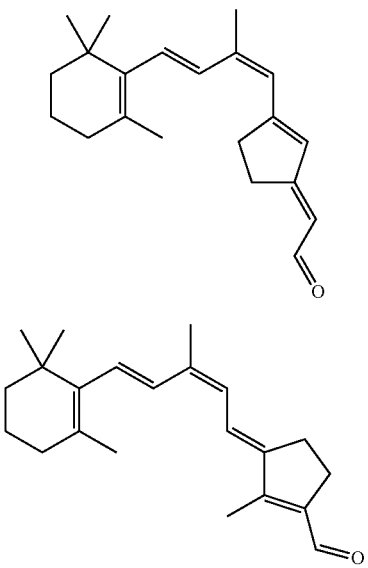

In other embodiments, the synthetic retinoid can be a 9-cis-ring-fused derivative, such as, for example, those shown in formulae X-XII.

In yet another embodiment, the synthetic retinoid is of the following formula XIII.

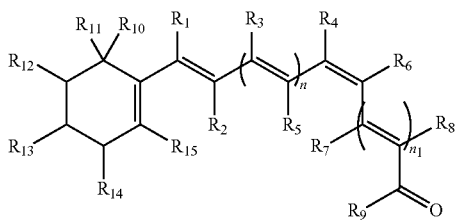

Each of R1 to R15 can be independently selected from hydrogen, alkyl, branched alkyl, halogen, hydroxyl, hydroxyalkyl, amine, amide, a heteroatom, or the like. Suitable alkyls include, for example, methyl, ethyl, propyl, substituted alkyl (e.g., alkyl with hydroxyl, hydroxyalkyl, amine, amide), or the like. Suitable branched alkyl can be, for example, isopropyl, isobutyl, substituted branched alkyl, or the like. Suitable halogens include, for example, bromine, chlorine, fluorine, or the like. Suitable heteroatoms include, for example, sulfur, silicon, and fluoro- or bromo-substitutions. Suitable substituted alkyls and substituted branch alkyls include, for example, alkyls and branched alkyls substituted with oxygen, hydroxyl, nitrogen, amide, amine, halogen, heteroatom or other groups. Each of n and $n_1$ can be independently selected from 1, 2, or 3 alkyl, alkene or alkylene groups, with the proviso that the sum of the n and $n_1$ is at least 1. In addition, R11-R12 and/or R13-R14 can comprise an alkene group in the cyclic carbon ring. In certain embodiments, R5 and R7 together can form a cyclo-alkyl, such as a five, six, seven or eight member cyclo-alkyl or substituted cyclo-alkyl, such as, for example, those shown in formulae VII, VIII, X, XI and XII.

In additional embodiments, the synthetic retinoid also can be 9-cis-retinal. Alternatively, 11-cis-retinal can be used.

Methods of making synthetic retinoids are disclosed in, for example, the following references: *Anal. Biochem.* 272: 232-42 (1999); *Angew. Chem.* 36:2089-93 (1997); *Biochemistry* 14:3933-41 (1975); *Biochemistry* 21:384-93 (1982); *Biochemistry* 28:2732-39 (1989); *Biochemistry* 33:408-16 (1994); *Biochemistry* 35:6257-62 (1996); *Bioorganic Chemistry* 27:372-82 (1999); *Biophys. Chem.* 56:31-39 (1995); *Biophys. J.* 56:1259-65 (1989); *Biophys. J.* 83:3460-69 (2002); *Chemistry* 7:4198-204 (2001); *Chemistry* (Europe) 5:1172-75 (1999); *FEBS* 158:1 (1983); *J. American Chem. Soc.* 104:3214-16 (1982); *J. Am. Chem. Soc.* 108:6077-78 (1986); *J. Am. Chem. Soc.* 109:6163 (1987); *J. Am. Chem. Soc.* 112:7779-82 (1990); *J. Am. Chem. Soc.* 119:5758-59 (1997); *J. Am. Chem. Soc.* 121:5803-04 (1999); *J. American Chem. Soc.* 123:10024-29 (2001); *J. American Chem. Soc.* 124:7294-302 (2002); *J. Biol. Chem.* 276:26148-53 (2001); *J. Biol. Chem.* 277:42315-24 (2004); *J. Chem. Soc.—Perkin T.* 1:1773-77 (1997); *J. Chem. Soc.—Perkin T.* 1:2430-39 (2001); *J. Org. Chem.* 49:649-52 (1984); *J. Org. Chem.* 58:3533-37 (1993); *J. Physical Chemistry B* 102:2787-806 (1998); *Lipids* 8:558-65; *Photochem. Photobiol.* 13:259-83 (1986); *Photochem. Photobiol.* 44:803-07 (1986); *Photochem. Photobiol.* 54:969-76 (1991); *Photochem. Photobiol.* 60:64-68 (1994); *Photochem. Photobiol.* 65:1047-55 (1991); *Photochem. Photobiol.* 70:111-15 (2002); *Photochem. Photobiol.* 76:606-615 (2002); *Proc. Natl Acad. Sci. USA* 88:9412-16 (1991); *Proc. Natl Acad. Sci. USA* 90:4072-76 (1993); *Proc. Natl Acad. Sci. USA* 94:13442-47 (1997); and *Proc. R. Soc. Lond. Series B, Biol. Sci.* 233 (1270): 55-76 1988) (the disclosures of which are incorporated by reference herein).

Opsin-binding synthetic retinoids can be identified by an expression system expressing a mutant opsin protein. Suitable expression systems can include, for example, in vitro or in vivo systems. Suitable in vitro systems include for example, coupled transcription-translation systems. Suitable in vivo systems include, for example, animal models and cells expressing a mutant opsin protein. For example, cells of a vertebrate visual system can be adapted for culture in vitro, or recombinant cell lines expressing an opsin protein can be used.

Suitable non-human animal models include rat, mouse, primate systems. Such animal models can be prepared, for example, by promoting homologous recombination between a nucleic acid encoding an opsin in its chromosome and an exogenous nucleic acid encoding a mutant opsin. In one aspect, homologous recombination is carried out by transforming embryo-derived stem (ES) cells with a vector containing an opsin gene, such that homologous recombination occurs, followed by injecting the ES cells into a blastocyst, and implanting the blastocyst into a foster mother, followed by the birth of the chimeric animal (see, e.g., Capecchi, *Science* 244:1288-92 (1989)). The chimeric animal can be bred to produce additional transgenic animals.

Also, recombinant cell lines expressing a mutant opsin protein can be used. The cell lines are typically stable cell lines expressing the mutant opsin protein. Synthetic retinoid can be added to the cell culture media, and the cells are cultured for a suitable period of time to allow the production of opsin/rhodopsin. Opsin and/or rhodopsin can be isolated (e.g., by immunoaffinity). Isolated protein samples are examined to determine the amount of pigment formed, and absorbance maxima.

Recombinant cell lines expressing mutant opsin protein can be prepared by, for example, introducing an expression construct encoding a mutant opsin protein into a suitable cell line. Methods of introducing nucleic acids into vertebrate cells are disclosed in, for example, Sambrook et al., *Molecular Cloning: A Laboratory Manual*, Cold Spring Harbor Laboratory Press (Cold Spring Harbor, N.Y., 2001) (the disclosure of which is incorporated by reference herein). The expression construct typically includes a promoter operably linked to a nucleic acid encoding a mutant opsin protein, and optionally a termination signal(s). Nucleic acids encoding opsin can be obtained, for example, by using information from a database (e.g., a genomic or cDNA library), by polymerase chain reaction, or the like. For example opsin encoding nucleic acids can be obtained by hybridization. (See generally Sambrook et al. (supra).) In a specific embodiment, an opsin encoding nucleic acid can be obtained by hybridization under conditions of low, medium or high stringency.

In certain embodiments, opsin encoding nucleic acids can be obtained under conditions of high stringency hybridization. By way of example, and not limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5-20×$10^6$ cpm of $^{32}$P-labeled probe. Washing of filters is done at 65° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which can be used are well known in the art. (See generally Sambrook et al. (supra).)

The expression construct can optionally include one or more origins of replication and/or selectable marker(s) (e.g., an antibiotic resistance gene). Suitable selectable markers include, for example, those conferring resistance to ampicillin, tetracycline, neomycin, G418, and the like. Suitable cells lines include, for example, HEK293 cells, T-REx™-293 cells, CHO cells and other cells or cell lines.

The UV-visible spectra of rhodopsin mutants (comprising mutant opsin and a synthetic retinoid) can be monitored to determine whether the synthetic retinoid has formed a Schiff base with the mutant opsin protein. For example, acid-denatured, purified protein can be analyzed to determine whether an absorbance maxima of approximately 440 nm is present, providing evidence that the synthetic retinoid forms a Schiff base with the mutant opsin protein. In additional embodiments, hydroxylamine treatment can be used to confirm the Schiff's base is sequestered from the external environment (infra).

Suitable opsin-binding synthetic retinoids also can be selected by molecular modeling of rhodopsin and opsin mutants. The coordinates for rhodopsin crystal structure are available from the Protein Data Bank (1HZX) (Teller et al., *Biochemistry* 40:7761-72 (2001)). The effects of amino acid substitutions on the structure of rhodopsin, and on the contacts between opsin and 11-cis-retinal, or a synthetic retinoid, can be determined by molecular modeling.

In an exemplary embodiment, the coordinates for the rhodopsin crystal structure from the Protein Data Bank (1HZX) (Teller et al., *Biochemistry* 40:7761-72 (2001)) are used to generate a computer model. As appropriate, amino acid substitutions can be introduced into the rhodopsin crystal structure. The addition of hydrogen atoms and optimization can be done, for example, using Insight II (InsightII release 2000, Accelrys, Inc., San Diego, Calif.). Crystallographic water can be removed, and water molecules introduced based on the accessible space in the extracellular region. Typically, no minimization is performed before water is added. A water layer (e.g., 5 Å thick) can be used to coat the extracellular part of rhodopsin as well as residues in contact with polar phospholipids heads. All of the water molecules can be allowed to move freely, as is the extracellular half of rhodopsin, with retinal. If no water cap is put on the cytoplasmic part of rhodopsin, this part of the molecule can be frozen to prevent degradation of the model.

In certain embodiments, a water cap is put on the extracellular part of rhodopsin (together with that part buried in membrane in contact with polar heads of phospholipids). Water and the extracellular part of rhodopsin can be allowed to move and the movement modeled at any suitable frequency. For example, the movement of the modeled rhodopsin can be modeling at 100 ps simulations.

Opsin-binding synthetic retinoids are contacted with a mutant opsin protein under conditions suitable and for a period of time sufficient for the formation of a mutant opsin protein/synthetic retinoid complex. The stability of the mutant opsin/synthetic retinoid complex can be determined by methods described herein or as known to the skilled artisan. The mutant opsin in the mutant opsin/synthetic retinoid complex is stabilized when it exhibits increased stability (e.g., increased affinity for the synthetic retinoid as compared with 11-cis-retinal, is less sensitive to hydroxylamine, exhibits less accumulation in aggresomes, or the like), as compared with the mutant opsin protein associated with 11-cis-retinal.

In certain embodiments, the mutant opsin protein is Pro23His opsin (i.e., having a proline to histidine amino acid substitution in opsin protein at position 23). The opsin-binding synthetic retinoid can be contacted with the mutant opsin protein in vitro or in vivo. For example, the mutant opsin protein can be synthesized in an in vitro translation system (e.g., a wheat germ or reticulocyte lysate expression system) and the synthetic retinoid added to the expression system. In additional embodiments, the mutant opsin protein can be contacted with the mutant opsin protein ex vivo, and then the complex can be administered to a vertebrate eye.

As used herein, "prophylactic" and "prophylactically" refer to the administration of a synthetic retinoid to prevent deterioration or further deterioration of the vertebrate visual system, as compared with a comparable vertebrate visual system not receiving the synthetic retinoid. The term "restore" refers to a long-term (e.g., as measured in weeks or months) improvement in photoreceptor function in a vertebrate visual system, as compared with a comparable vertebrate visual system not receiving the synthetic retinoid. The term "stabilize" refers to minimization of additional degradation in a vertebrate visual system, as compared with a comparable vertebrate visual system not receiving the synthetic retinoid.

Opsin-binding synthetic retinoids can be administered to a vertebrate eye having mutant opsin protein. In certain aspects, the vertebrate eye is characterized as having an inherited retinal disease, such as, for example, Retinitis Pigmentosa, in which there is a defect in opsin gene or opsin protein. In certain embodiments, the mutant opsin protein has a P23H amino acid substitution. In other embodiments, the mutant opsin protein has an amino acid substitution or other mutation in the N-terminal plug of opsin. The synthetic retinoid binds to and stabilizes the opsin protein. Typically, the stabilized opsin protein can be incorporated into the membrane rather than forming an aggregate.

Synthetic retinoids can be administered to human or other non-human vertebrates. Synthetic retinoids can be delivered to the eye by any suitable means, including, for example, oral or local administration. Modes of local administration can include, for example, eye drops, intraocular injection or periocular injection. Periocular injection typically involves injection of the synthetic retinoid into the conjunctiva or to the tennon (the fibrous tissue overlying the eye). Intraocular injection typically involves injection of the synthetic retinoid into the vitreous. In certain embodiments, the administration is non-invasive, such as by eye drops or oral dosage form.

Synthetic retinoids can be formulated for administration using pharmaceutically acceptable vehicles as well as techniques routinely used in the art. A vehicle is selected according to the solubility of the synthetic retinoid. Suitable ophthalmological compositions include those that are administrable locally to the eye, such as by eye drops, injection or the like. In the case of eye drops, the formulation can also optionally include, for example, isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8.

For injection, the synthetic retinoid can be provided in an injection grade saline solution, in the form of an injectable liposome solution, or the like. Intraocular and periocular injections are known to those skilled in the art and are described in numerous publications including, for example, *Ophthalmic Surgery: Principles of Practice*, Ed., G. L. Spaeth, W. B. Sanders Co., Philadelphia, Pa., U.S.A., pages 85-87 (1990).

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington "Pharmaceutical Sciences"*, 17 Ed., Gennaro (ed.), Mack Publishing Co., Easton, Pa. (1985)).

The doses of the synthetic retinoids can be suitably selected depending on the clinical status, condition and age of the subject, dosage form and the like. In the case of eye drops, a synthetic retinoid can be administered, for example, from about 0.01 mg, about 0.1 mg, or about 1 mg, to about 25 mg, to about 50 mg, to about 90 mg per single dose. Eye drops can be administered one or more times per day, as needed. In the case of injections, suitable doses can be, for example, about 0.0001 mg, about 0.001 mg, about 0.01 mg, or about 0.1 mg, to about 10 mg, to about 25 mg, to about 50 mg, or to about 90 mg of the synthetic retinoid, one to four times per week. In other embodiments, about 1.0 to about 30 mg of synthetic retinoid can be administered one to three times per week.

Oral doses can typically range from about 1.0 to about 1000 mg, one to four times, or more, per day. An exemplary dosing range for oral administration is from about 10 to about 250 mg one to three times per day.

The following examples are provided merely as illustrative of various aspects of the invention and shall not be construed to limit the invention in any way.

EXAMPLES

Example 1

The present study demonstrates that P23H-opsin can be induced to properly fold by providing cells with a seven-membered ring variant of 11-cis-retinal during opsin biosynthesis. The affinity and selectivity of mutant opsin for 11-cis-7-ring retinal can be explained based on the crystal structure of rhodopsin.

Methods and Materials

Synthesis of 1-cis-7-Ring Retinals:

Synthesis of 11-cis-7-ring retinals was performed as described previously with some modifications (Fujimoto et al., *Chirality* 14:340-46 (2002); Akito et al., *J. Am. Chem.* 102:6370-72 (1980); Caldwell et al., *J. Org. Chem.* 58:3533-37 (1993). All of the reactions were performed in a dried nitrogen atmosphere unless otherwise specified. 2-Cycloheptenone was first converted into allyl acetate by N-bromosuccinimide bromination in $CCl_4$ followed by treatment with KOAc in hexamethylphosphoramide. Purified 4-acetoxy-2-cycloheptenone (46% from 2-cycloheptenone) was subjected to a Horner-Emmons reaction with diethyl (2-cyanoethyl)phosphonate, which gave an isomeric mixture of two trans/cis (E/Z) cyanoacetates in a 2:1 ratio. The mixture was hydrolyzed with $K_2CO_3$ in $MeOH:H_2O$ (5:1), and then the hydroxy group of the resulting allylic alcohol was protected with tert-butyldimethylsilyl chloride in pyridine (80% from cycloheptenonyl acetate). The resulting cyano compound was reduced with diisobutylaluminium hydride in $CH_2Cl_2$ to an aldehyde and purified by flash chromatography on a silica gel (63%). β-Cyclocitral was reduced with. $NaBH_4$ to β-cyclogeraniol and then reacted with triphenylphosphine hydrobromide in MeOH over 3 days to afford β-cyclogeranyltriphenylphosphonium bromide after the removal of solvent and drying of the residue in vacuum. Wittig reaction of the silylated aldehyde with an excess of phosphonium salt in the presence of potassium tert-butoxide and a catalytic amount of 18-crown-6 in methylene chloride at ambient temperature afforded protected cyclic alcohol in 75% yield. The tert-butyldimethylsilyl protecting group was removed by treatment with tetrabutylammonium fluoride in dry THF, and the resulting alcohol was oxidized with $MnO_2$ in $CH_2Cl_2$ to a mixture of two (E/Z) cyclic ketones (2:1 ratio) in 96% yield. This mixture was condensed with triethyl phosphonoacetate under Homer-Emmons conditions, followed by lithium aluminum hydride reduction of the resulting isomeric mixture of ethyl 7-ring retinoates and oxidation of retinols with $MnO_2$ (86%) in $CH_2Cl_2$.

The following isomers were used: isomer 1 (FIG. 1B), 9,11,13-tri-cis-7-ring retinal: 1.04 (s, 6H, 2×$CH_3$-1), 1.45-1.50 (m, 2H, $CH_2$-2), 1.59-1.67 (m, 2H, $CH_2$-3), 1.74 (s, 3H, $CH_3$-5), 1.90 (m, 2H, J 6.74 Hz, $CH_2$-22), 1.97 (s, 3H, $CH_3$-9), 2.03 (t, 2H, $CH_2$-4), 2.46 (t, 2H, J 7.26 Hz $CH_2$-20), 2.51 (t, 2H, J 6.74 Hz $CH_2$-21), 5.78 (d, 1H, J 7.78 Hz, H-14), 6.20 (d, 1H, J 11.42 Hz, H-7), 6.54 (d, 1H, J 11.42 Hz, H-8), 6.95 (d, 1H, J 16.08 Hz, H-12), 7.08 (d, 1H, J 16.08 Hz, H-11), 10.11 (d, 1H, J 7.78 Hz, H-15); isomer 2 (FIG. 1B), 11,13-di-cis-7-ring retinal: 1.04 (s, 6H, 2×$CH_3$-1), 1.47-1.50 (m, 2H, $CH_2$-2), 1.60-1.67 (m, 2H, $CH_2$-3), 1.73 (s, 3H, $CH_3$-5), 1.86 (m, 2H, J 6.74 Hz, $CH_2$-22), 2.00 (s, 3H, $CH_3$-9), 2.04 (t, 2H, $CH_2$-4), 2.45 (t, 2H, J 7.27 Hz $CH_2$-20), 2.54 (t, 2H, J 6.74 Hz $CH_2$-21), 5.79 (d, 1H, J 7.78

Hz, H-14), 6.32 (d, 1H, J 16.08 Hz, H-7), 6.52 (d, 1H, J 16.08 Hz, H-8), 7.02 (m, 2H, H-11, H-12), 10.12 (d, 1H, J 7.78 Hz, H-15); isomer 3 (FIG. 1B), 11-cis-7-ring retinal: 1.04 (s, 6H, 2×CH$_3$-1), 1.44-1.52 (m, 2H, CH$_2$-2), 1.57-1.67 (m, 2H, CH$_2$-3), 1.74 (s, 3H, CH$_3$-5), 1.86 (m, 2H, J 6.74 Hz, CH$_2$-22), 2.00 (s, 3H, CH$_3$-9), 2.04 (t, 2H, CH$_2$-4), 2.58 (t, 2H, J 6.75 Hz CH$_2$-20), 2.87 (t, 2H, J 6.75 Hz CH$_2$-21), 5.93 (d, 1H, J 8.3 Hz, H-14), 6.22 (d, 1H, J 11.42 Hz, H-12), 6.32 (d, 1H, J 16.08 Hz, H-7), 6.52 (d, 1H, J 16.08 Hz, H-8), 6.91 (s, 1H, J 11.42 Hz, H-11), 10.03 (d, 1H, J 7.79 Hz, H-15); and isomer 4 (FIG. 1B), 9,11-di-cis-7-ring retinal: 1.04 (s, 6H, 2×CH$_3$-1), 1.44-1.52 (m, 2H, CH$_2$-2), 1.57-1.67 (m, 2H, CH$_2$-3), 1.74 (s, 3H, CH$_3$-5), 1.86 (m, 2H, J 6.74 Hz, CH$_2$-22), 2.00 (s, 3H, CH$_3$-9), 2.04 (t, 2H, CH$_2$-4), 2.58 (t, 2H, J 6.75 Hz CH$_2$-20), 2.87 (t, 2H, J 6.75 Hz CH$_2$-21), 5.93 (d, 1H, J 8.3 Hz, H-14), 6.17 (d, 1H, J 11.41 Hz, H-12), 6.21 (d, 1H, J 16.08 Hz, H-7), 6.53 (d, 1H, J 16.08 Hz, H-8), 6.98 (s, 1H, J 11.41 Hz, H-11), 10.03 (d, 1H, J 7.78 Hz, H-15).

Cell Lines and Growth Conditions:

For the construction and selection of tetracycline-inducible opsin cell lines, an Invitrogen T-REx™ system was used. Briefly, nucleic acids encoding wild-type opsin and the P23H mutant were excised as EcoRI-NotI fragments from pMT4 and then cloned into the EcoRI-NotI site within the polylinker of pcDNA4. Using opsin-specific forward and reverse primers, the entire gene was sequenced for verification. These plasmids were then separately transfected by calcium-phosphate precipitation into T-REx™-293 cells that already stably expressed the tetracycline repressor; these cells were routinely grown under blasticidin selection. After transfection, zeocin was added to the culture medium, and surviving colonies of cells were isolated and subsequently expanded into larger 6-well plates. Each of these clones was exposed to tetracycline, and 48 hours after induction, the cells were harvested and solubilized with 1% DM. Separately, uninduced cells were also solubilized. The samples were run on SDS-PAGE and immunoblotted with the monoclonal antibody 1D4. Cell lines were chosen on the basis of production of the least amount of opsin (i.e., nondetectable opsin levels on immunoblots) in the absence of tetracycline and moderate amounts of opsin in the presence of the drug. HEK293 cells were grown in Dulbecco's modified Eagle's medium containing high glucose (Invitrogen) at 37° C. in the presence of 5.0% CO$_2$. In all of the studies, the cells were harvested after 48 hours of induction with tetracycline (1 µg/ml).

Cell Culture and Regeneration:

The cells were washed three times with PBS, harvested, and incubated with different analogs of 11-cis-retinal (50 µM) for 45 minutes at 4° C. The cells were then lysed with 1.0% n-dodecyl-maltoside (DM) (Anatrace) in the presence of protease inhibitors (complete protease inhibitor mixture tablets; Roche Molecular Biochemicals) and centrifuged at 36,000 rpm in a Beckman ultracentrifuge for 30 minutes at 4° C. The supernatant was incubated with 1D4-coupled CNBr-activated Sepharose 4B (Pharmacia Corp.) beads overnight. The beads were then washed three times with PBS containing 0.1% DM. Bound pigments were eluted off the beads using 0.1 mM synthetic peptide (last 9 amino acid residues of the C terminus of rhodopsin) in 0.1% DM. In studies when retinoids (50 µM) were added during biosynthesis, a Me$_2$SO solution of retinoids (10 µl of 100 mM) was added directly to the cell culture medium after 2 and 24 hours of induction. The cells were harvested at 48 hours and lysed with 1.0% DM. Pigment was purified by immunoaffinity chromatography. The UV-visible spectra of the eluted pigment samples were then recorded on a Perkin Elmer Lambda 800 UV-visible spectrophotometer in the range of 250-650 nm.

SDS Gel Electrophoresis and Immunoblotting:

The samples were loaded on 10% SDS-polyacrylamide gels and transferred to Immobilon-NC membrane (Millipore) according to established protocols. The membranes were blocked with blocking buffer (Licor) for 1 hour and incubated at room temperature with 1D4 antibody (1:1000) for 1 hour. The membranes were then washed with PBS containing 0.1% Tween 20 and then incubated for 1 hour at room temperature with IRDye800™-conjugated affinity purified goat anti-mouse IgG (Licor), diluted 1:5000. The membranes were then washed with PBS containing Tween 20 and scanned using an Odyssey Infrared imager (Licor).

Glycosylation Status:

Purified 7-rhodopsin and 7-P23H-rhodopsin (rhodopsin and P23H-rhodopsin regenerated with 11-cis-7-ring retinal, respectively) were treated with N-glycanase according to the manufacturer's recommendations (Glyko). The samples were incubated at 37° C. for 16 hours and then loaded onto a 10% polyacrylamide gel. The immunoblots were developed as described above.

Photosensitivity Studies:

Whole cells expressing wild-type and P23H-opsin treated with 11-cis-7-ring retinals were harvested and exposed for 20 minutes to light emitted from a Fiber-Lite, MI 150, High Intensity Illuminator (Dolan-Jenner). The cells were then washed and then lysed with 1.0% DM as described above. In a separate study, immunoaffinity purified 7-rhodopsin and 7-P23H-rhodopsin samples were exposed to light from Fiber-Lite, and UV-visible spectra were recorded at different times.

Hydroxylamine Sensitivity:

Whole cells expressing wild-type and P23H-opsin treated with 11-cis-7-ring retinals were harvested and treated with 500 mM neutral solution of hydroxylamine for 45 min. The cells were thoroughly washed with PBS to remove all traces of hydroxylamine. Rhodopsin was then purified, and spectra were taken. In a separate study, purified 7-rhodopsin and 7-P23H-rhodopsin were treated with 20 mM neutral hydroxylamine, and UV-visible spectra were recorded at different times.

Thermostability of Pigments and Acid Hydrolysis:

Purified 7-rhodopsin and 7-P23H-rhodopsin were incubated at 37° C., and the spectra were recorded at indicated times. In acid treatment studies, purified 7-rhodopsin and 7-P23H-rhodopsin were treated with 100 mM sulfuric acid, and spectra were recorded.

HPLC Analysis of Retinoids:

A 450 µl aliquot of either purified 7-rhodopsin, purified 7-P23H-rhodopsin, or cell medium were treated with 50 µl of 10% SDS and 100 µl of 1 M NH$_2$OH (freshly prepared, pH 7.5). The mixture was kept at room temperature for 30 min, and then 400 µl of MeOH and 400 µl of hexane were added. The mixture was shaken on a vortex for 5 minutes and centrifuged at 14,000 rpm to separate layers. The hexane layer was collected. Another 400 µl of hexane was added to the aqueous layer, and extraction was repeated. Combined hexane layers were dried down and redissolved in 120 µl of hexane, and 100 µl fractions were analyzed by normal phase HPLC as previously described.

Immunocytochemistry:

HEK293 cells expressing wild-type rhodopsin or P23H-opsin under a tetracycline-inducible promoter were cultured in Dulbecco's modified Eagle's medium (Invitrogen). The cells were attached to glass bottom microwell dishes (Mat- Tek Corp.) with Cell-Tak (Becton Dickinson Labware). Expression of opsin or P23H-opsin was induced by the addition of 1 μg/ml tetracycline as recommended by the manufacturer's protocol (Invitrogen). The cells were treated with 50 μM 11-cis-7-ring retinal 2 hours after induction. The cells were harvested after 24 hours and fixed with 4% paraformaldehyde (Fisher) in PBS (136 mM NaCl, 11.4 mM sodium phosphate, pH 7.4) for 10 minutes and washed by PBS. To block nonspecific labeling, the cells were incubated in 1.5% normal goat serum (Vector Lab., Inc.) in PBST (136 mM NaCl, 11.4 mM sodium phosphate, 0.1% Triton X-100, pH 7.4) for 15 minutes at room temperature. The cells were incubated overnight at 4° C. in purified 1D4 antibody diluted with PBST. The sections were rinsed in PBST and incubated with indocarbocyanine (Cy3)-conjugated goat anti-mouse IgG (Jackson ImmunoResearch Lab., Inc.) and Hoechst 33342 dye (Molecular Probes). The cells were rinsed in PBST and mounted in 50 μl of 2% 1,4-diazabicyclo-[2.2.2] octane (Sigma) in 90% glycerol to retard photobleaching. For confocal imaging, the cells were analyzed on a Zeiss LSM510 laser scanning microscope (Carl Zeiss, Inc.).

Protein Simulation and Modeling:

Coordinates for rhodopsin were taken from the Protein Data Bank (1HZX) (Teller et al., *Biochemistry* 40:7761-72 (2001). The addition of hydrogen atoms and all of the optimizations were done in Insight II (InsightII release 2000, Accelrys, Inc., San Diego, Calif.). Crystallographic water was removed, and water molecules were introduced based on the accessible space in the extracellular region. No minimization was performed before water was added.

A water layer (5 Å thick) was used to coat the extracellular part of rhodopsin as well as residues in contact with polar phospholipids heads. All of the water molecules were allowed to move freely, as was the extracellular half of rhodopsin, which contains P23H and retinal. Because no water cap was put on the cytoplasmic part of rhodopsin, this part of the molecule was frozen to prevent degradation of the model.

Results

The chromophore of rhodopsin, 11-cis-retinal, plays a central role in the photoactivation process and is also important for the stabilization of the receptor. For example, rhodopsin is stable for months in mild detergents, although opsin precipitates in a few hours. The chromophore may also induce a proper folding of rhodopsin mutants. The P23H amino acid substitution may destabilize the native chromophore-accepting conformation of opsin, leading to aberrant folding and subsequent aggregation. However, an analog of 11-cis-retinal may facilitate native-like folding of P23H-opsin and therefore play the role of pharmacological chaperone. Recently, wild-type opsin was regenerated with 11-cis-7-ring retinal (7-rhodopsin), containing a chromophore with a seven-membered ring to prevent isomerization around the C11=C12 double bond (FIG. 1B), is very stable in vivo and in vitro. In contrast, bleaching of the wild-type opsin regenerated with 11-cis-6-ring retinal (6-rhodopsin), which contains a more rigid chromophore, produces multiple isomers with modest changes in protein conformations. These results reveal that 11-cis-7-ring retinals, particularly isomer 3 (FIG. 1B), are easily accepted into the binding site of opsin and provide additional contact sites by virtue of the seven-membered ring and the 9-methyl group with the protein moiety. Because of its intrinsic flexibility, this analog could potentially influence/affect protein folding during biosynthesis, which is particularly important for those mutant proteins that fold less efficiently. The binding pocket of wild-type opsin adopts specific conformations that allow it to bind preferentially certain retinoids.

11-cis-7-Ring Retinal Chaperone Folding of P23H-Opsin:

Rhodopsin is regenerated with 11-cis-7-ring retinals in the harvested membranes (FIG. 2B), whereas only a small amount of pigment was formed when membranes containing P23H-opsin were treated with 11-cis-retinal, 11-cis-6-ring retinal, or 11-cis-7-ring retinal after the cells were harvested (FIG. 2B). If the mutant proteins are structurally unstable, it was proposed that the addition of retinal during the course of protein biosynthesis might induce a more native-like folding of the protein and its subsequent stabilization.

Figures 2C, 2D:
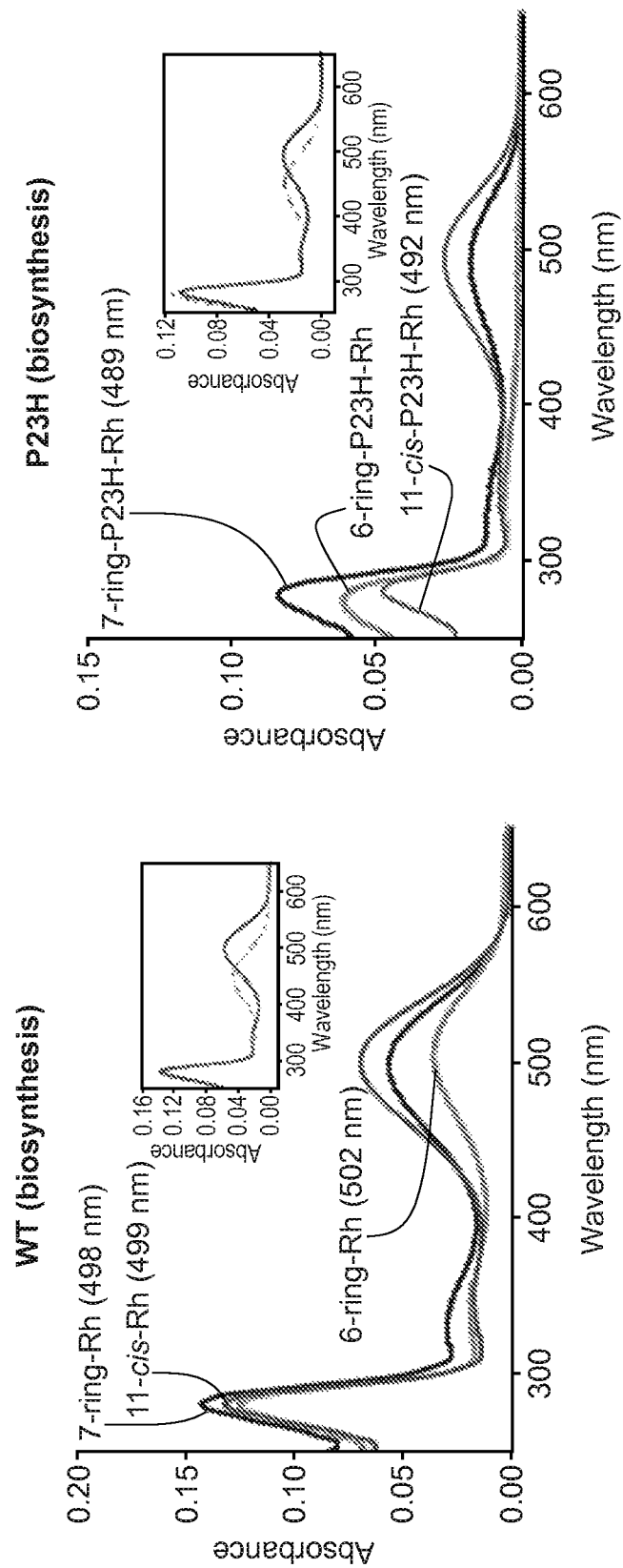

The first studies utilized 11-cis-locked versions of 11-cis-retinal in stable cell lines expressing wild-type and P23H-opsin. The UV-visible spectra of the immunoaffinity purified samples from 11-cis-6- or 11-cis-7-ring retinals provided to the cells during biosynthesis showed that both retinals recombined with wild-type opsin (FIG. 2C). Supporting this prediction, P23H-opsin formed significant amounts of pigment when 11-cis-7-ring retinal was added during biosynthesis (FIG. 2D). The max of the pigment was approximately 490±3 nm, unlike the wild-type protein (with a max of approximately 500±3 nm) (FIGS. 2, C and D). The UV-visible spectra with a max of approximately 440 nm of acid-denatured purified 7-P23H-rhodopsin (FIG. 2D, inset) provided evidence that the chromophore forms a Schiff base with rescued P23H-opsin. No significant pigment was seen when 11-cis-6-ring retinal, which is photoisomerable along C9- and C13-C=C double bonds, was added to P23H-opsin-expressing cells (FIG. 2D). Furthermore, 11-cis-9-demethyl-7-ring retinal was also ineffective in pigment formation with P23H-opsin. These studies illustrate unique specificity of the binding interaction between 11-cis-7-ring retinal and P23H-opsin.

Immunoblots showed that the rescued P23H-opsin had a high molecular weight and a Golgi-associated glycosylation pattern similar to the wild-type protein, suggesting that the protein is sufficiently folded to proceed along the secretory pathway. This is in striking contrast to P23H-opsin that was not treated with 11-cis-7-ring retinal during P23H-opsin biosynthesis. Purified 7-rhodopsin and 7-P23H-rhodopsin were efficiently deglycosylated by N-glycanase, and the mutant protein spontaneously aggregated, forming high molecular weight aggregates).

In control studies, 9-cis-retinal and 11-cis-retinal were tested for proper folding of P23H-opsin. It should also be noted that 9-cis-retinal promoted transport of P23H-opsin to the cell surface. 11-cis-retinal was also observed to induce the in vivo folding and stabilization of P23H-opsin forming visual pigments (499 nm and 492 nm, for rhodopsin and P23H-rhodopsin, respectively) (FIGS. 2, C and D). Moreover, these pigments also acquired a mature state of glycosylation. 11-cis-retinoids are unstable in vitro and in vivo and rapidly undergo "reverse isomerization.". Therefore, locked analogs were used throughout the rest of this study.

Properties and Stability of 7-P23H-Rhodopsin:

When the mixture of the four 7-ring retinal isomers (FIG. 1B) was added to cells expressing opsin and P23H-opsin during biosynthesis, both wild-type opsin and P23H-opsin selectively bound only isomer 3. These observations further support the extraordinary specificity of wild-type and P23H-opsin for binding this 11-cis-retinal isomer. Addition of 11-cis-retinal to cell membranes containing either wild-type or P23H-opsin that were already treated with the 11-cis-7-ring retinal during their biosynthesis did not lead to its substitution after photobleaching, as measured spectrophotometrically and by retinoid analysis of the bound chromophores. 7-Rhodopsin, purified in the detergent, is stable to light (FIG. 3A), whereas purified 7-P23H-rhodopsin undergoes bleaching under the same conditions (FIG. 3B). In contrast, both rhodopsins are stable in the membranes of HEK293 cells (FIGS. 3, C and D). This result suggests that, in detergent, the chromophore in 7-P23H-rhodopsin is more flexible, thus allowing photoisomerization. The mechanism by which 7-P23H-rhodopsin undergoes bleaching in detergent most likely involves isomerization of isomer 3 to three other isomers and its subsequent hydrolysis. The membranes apparently stabilized 7-P23H-rhodopsin, thus preventing isomerization of its bound chromophore. In tissue culture samples, small amounts of non-rhodopsin-bound retinals eluted between 30 and 40 minutes and remained in equilibrium with the vast majority of retinols, governed by the redox potential of the cells.

To further characterize the rescued protein, the affinity bound 7-rhodopsin and 7-P23H-rhodopsin were eluted under conditions that selectively released only the folded form of the protein (10 mM phosphate, pH 6.0). The spectra of the eluates (FIGS. 2, E and F) and the corresponding immunoblots indicated that approximately 80% of 7-P23H-rhodopsin folded to form pigment. Additionally, immunoblots of these eluates demonstrated that both contained a mature glycosylated band and unglycosylated bands; however, only the material eluted at pH 6.0 had the Golgi-specific glycosylation pattern.

The structure of the rescued protein was also probed by determining its sensitivity to neutral hydroxylamine. 7-P23H-rhodopsin is resistant to hydroxylamine treatment when embedded in the lipid bilayer of HEK293 cells, suggesting that the rescued protein adopts a conformation that sequesters the Schiff base linkage within the protein and protects it from chemical modification. Unlike the purified wild-type protein, the mutant chromophore is accessible to hydroxylamine in detergent (0.1% DM), as evidenced by the formation of the retinaloximes (max=approximately 360 nm). These data imply that the structure of 7-P23H-rhodopsin is less tightly packed than that of the 7-rhodopsin. Finally, the temperature stability of the purified 7-rhodopsin and 7-P23H-rhodopsin was studied. There was no change in the amount of chromophore after incubation of 7-rhodopsin at either 4° C. or 37° C. However, for the rescued 7-P23H-rhodopsin, there is time-dependent thermal bleaching that is accelerated by increased temperature, with a half-life of approximately 4 minutes at 37° C. and 10 days at 4° C. in the detergent solution.

Localization of the Rescued 7-Locked-P23H-Rhodopsin:

Immunofluorescence microscopy demonstrated that P23H-opsin is retained intracellularly, predominantly in a perinuclear distribution with punctuated fluorescence consistent with aggresomes. In contrast, the rescued 7-P23H-rhodopsin is predominantly found in a diffuse pattern with significantly greater staining at the cell surface similar to the 7-rhodopsin and wild-type opsin, which are found predominantly at the plasma membrane. In summary, this result indicates that the rescued P23H-rhodopsin was not only correctly glycosylated and formed a pigment but was also correctly routed to the cell membranes.

Discussion

Protein Conformational Disorders:

Dominantly inherited diseases can result from (a) haploinsufficiency of a gene, e.g., as for the melanocortin-4 receptor; (b) constitutive activity (gain of function) in some opsin mutants or lack of activity because of somatic mutation; and (c) loss of function because of mutant protein misfolding and aggregation. The diseases caused by misfolded proteins are known as protein conformational disorders and include Alzheimer's disease, Huntington's disease, Parkinson's disease, diabetes insipidus, cystic fibrosis, prion disease, emphysema, dominant cataracts, and oculopharyngeal muscular dystrophy. Gene delivery is one method of correcting haploinsufficiency. Constitutive activity has been successfully blocked by reverse agonist-like compounds, and conformation and function can be rescued by small chemical agents. The medically most prevalent forms of dominant disorders are the protein conformational disorders. Although they are the most challenging to treat, some successes have been reported. Examples include the rescue of misfolded cystic fibrosis transmembrane regulator (CFTR) variant F508 and the Z-variant of 1-antitrypsin. In the instance of CFTR, the osmolytes glycerol and trimethylamino-oxide have been used. The protein acquires mature glycosylation and is transported to the cell surface where it pumps Cl ions. The chemical chaperone 4-phenylbutyric acid mediated a marked increase in secretion of $\alpha_1$-antitrypsin. Recent studies, however, suggest that the rescued protein is less stable than the wild-type. Other approaches to inducing the folding of proteins have been developed. For example, mini-chaperones that prevent β-sheet formation prevent toxic aggregation of amyloid-β found in Alzheimer's disease and the PrP protein associated with prion disease.

P23H Rescue:

This study demonstrates that P23H-opsin can be induced to properly fold and be stabilized with a seven-membered locked ring version of 11-cis-retinal, the inverse agonist of opsin. Furthermore, this model system provides a quantitative means to study the folding of this membrane protein. The rescued 7-P23H-rhodopsin contains a Schiff base linkage with Lys296, producing pigment with a max of approximately 490 nm (FIG. 2D) that can be used as a quantitative measure of the amount of correctly folded protein. Using chromatographic conditions that selectively elute the folded form of the protein, 11-cis-7-ring retinal leads to the rescue of approximately 80% of the P23H-opsin. This study also demonstrated that the rescued protein is not only folded but also proceeds along the secretory pathway. Like the wild-type protein, the rescued protein acquires the heterogeneous glycosylation associated with oligosaccharide processing within the Golgi apparatus. Clearly, the protein is of a sufficiently native-like conformation and is not sequestered by the cellular quality control apparatus, at least that which exists at the level of endoplasmic reticulum.

Furthermore, the rescued protein is structurally different from the wild-type protein. The detergent-purified protein is light-sensitive, displays thermal instability, and is sensitive to neutral hydroxylamine. The bleaching of detergent-solubilized 7-P23H-rhodopsin occurs because of isomerization of double bonds along the polyene chain of the chromophore producing a mixture of isomers. However, in the membranes of the HEK cells, 7-P23H-rhodopsin is stable, and therefore, it is expected this pigment will also be stable in vivo.

Chemical and Structural Considerations of the Rescue:

The mutant P23H protein is less stable because it is misfolded and is thus retained intracellularly. The rescue effect with 11-cis-7-ring retinal leads to increased amounts of the correctly folded mutant and is extraordinarily specific as shown by the lack of activity observed with several structural homologs (11-cis-9-demethyl-ring retinal and 11-cis-6-ring retinal). However, unlike the wild-type protein, purified 7-P23H-rhodopsin appears to be in a less compact conformation, as evidenced by its sensitivity to neutral hydroxylamine in detergent. It was also observed that the rescued protein spontaneously releases the locked retinoid over time. Previous studies have demonstrated that 11-cis-7-ring retinal is inherently more flexible than 11-cis-6-ring retinal. The rigidity of 11-cis-6-ring retinal may not allow the P23H-opsin binding pocket to accept this chromophore. Alternatively, P23H-opsin may bind 11-cis-6-ring retinal but that the resulting protein is less stable and maybe more susceptible to water-assisted hydrolysis of the Schiff base linkage, as it is in the case of 9-cis-retinal.

Figure 1B:
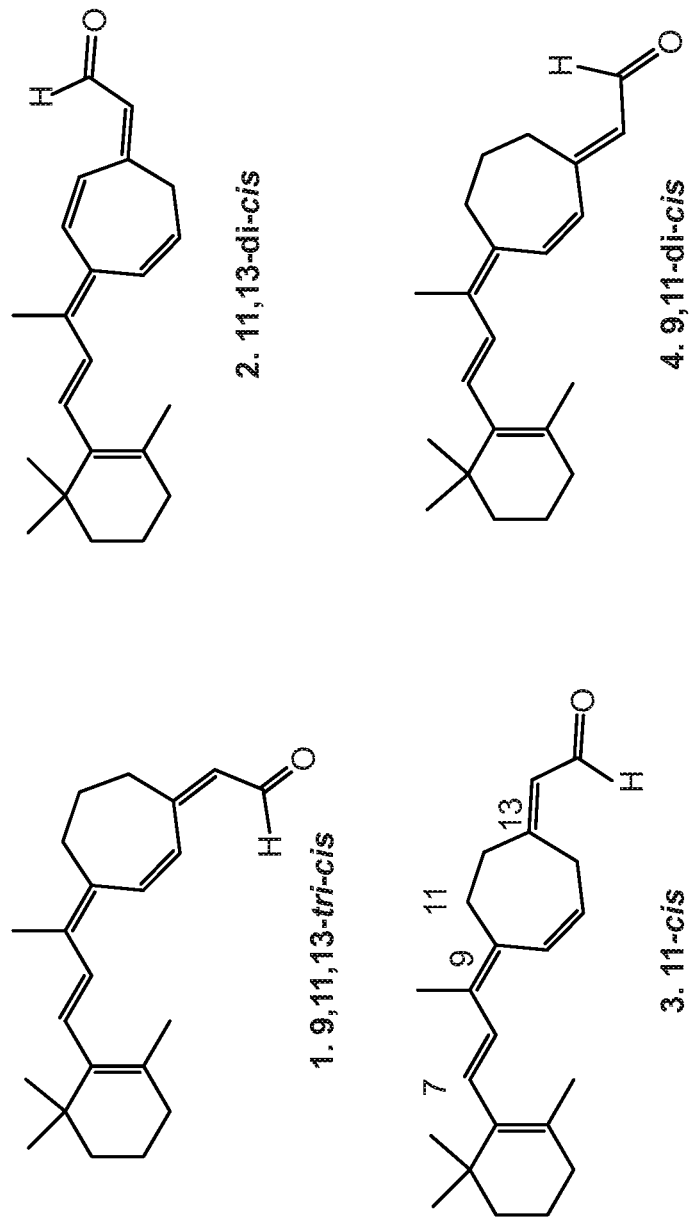

These molecular modeling studies provide an explanation for the defect caused by P23H mutation. Two alterations appear to be present in P23H mutant: (a) The mutation disrupts ionic interactions of Pro23, Gln182, and Glu184 on the tip of the plug between helices 4 and 5. Mutation of Pro to His leads to formation of conjugated hydrogen bonding that exposes the chromophore-binding site. This interaction stiffens the plug and possibly opens the binding site of opsin, allowing water to hydrolyze the Schiff base between the retinal chromophore and γ-amino group of Lys296. This prediction is consistent with a hipsochromic shift in the absorption maximum of the chromophore and accessibility to hydrolysis in the presence or absence of hydroxylamine. (b) There is a hydrophilic channel in the interior of the protein that could accommodate water molecules (FIG. 1E). In the model, rhodopsin was soaked with water on the external side, only including the part of the membranes that is charged and without constraints imposed on water molecules. During simulation, a route was established where water molecules drifted from one side to another (cytoplasmic). This route was along helix II and partly along helices I and III. The key residue facilitating this transport was Thr93 on helix II (close to Glu113). Collectively, these two effects may alter the electronic/dipole environment around the retinal, explaining the nearly 10-nm blue shift.

In summary, this study has shown using a cell culture model system that the retinitis pigmentosa mutant P23H-opsin can be induced to properly fold by providing cells with a seven-membered ring variant of 11-cis-retinal during opsin biosynthesis. Furthermore, the remarkable affinity and selectivity of mutant opsin for 11-cis-7-ring retinal on the basis of the crystal structure of rhodopsin.

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

It is claimed:

1. A method of treating retinitis pigmentosa due to expression of a mutant opsin protein with a substitution of proline 23 by histidine, comprising:
administering an opsin-binding synthetic retinoid to a human subject in need thereof, wherein the synthetic retinoid is administered in an amount effective to bind the mutant opsin protein to ameliorate loss of photoreceptor function;
wherein the synthetic retinoid is an 11-cis-7-ring retinal having the following formula:

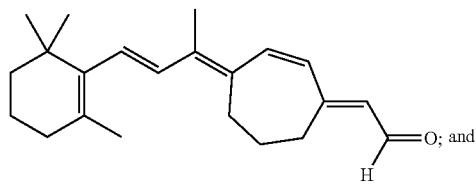 [SMILES: CC1=C(/C=C/C(C)=C2C=C/C(=C/C=O)CCC/2)C(C)(C)CCC1]

wherein the mutant opsin protein has improper protein folding and a reduced affinity for 11-cis-retinal.

2. The method of claim 1, wherein administering comprises orally administering the synthetic retinoid at a dose of between about 1-1000 mg, one to four times per day.

3. The method of claim 1, wherein administering comprises administering the synthetic retinoid by injection at a dose of between 0.001-90 mg per single dose.

4. The method of claim 3, wherein administering comprises administering the synthetic retinoid locally by intraocular injection or by periocular injection.

5. The method of claim 1, wherein administering comprises locally administering the synthetic retinoid more than once per day.

6. The method of claim 1, wherein administering comprises locally administering a dose of synthetic retinoid of between 0.01-90 mg per single dose.

7. The method of claim 6, wherein administering comprises administering the synthetic retinoid locally in the form of an eye drop.

8. The method of claim 1, wherein said contacting is effective to induce folding of the mutant opsin protein to form visual pigment.

9. A method of treating a human subject suffering from retinitis pigmentosa due to expression of a mutant opsin protein with a substitution of proline 23 by histidine, comprising:
treating, to improve photoreceptor function in the human subject, by contacting the mutant opsin protein, in an eye of the subject, with a synthetic retinoid to form an opsin/synthetic retinoid complex;
wherein the synthetic retinoid is an 11-cis-7-ring retinal having the following formula:

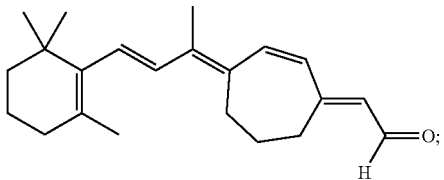 [SMILES: CC1=C(/C=C/C(C)=C2C=C/C(=C/C=O)CCC/2)C(C)(C)CCC1]

and wherein the mutant opsin protein has improper protein folding and a reduced affinity for 11-cis-retinal.

10. The method of claim 9, wherein said contacting is effective to induce folding of the mutant opsin protein to form visual pigment.

* * * * *